United States Patent
Hatakeyama

(10) Patent No.: US 8,311,621 B2
(45) Date of Patent: Nov. 13, 2012

(54) DEVICE FOR JUDGING DEGREE OF AWAKENING AND METHOD FOR JUDGING DEGREE OF AWAKENING

(75) Inventor: Yoshiyuki Hatakeyama, Susono (JP)

(73) Assignee: Toyota Jidosha Kabushiki Kaisha, Toyota (JP)

( * ) Notice: Subject to any disclaimer, the term of this patent is extended or adjusted under 35 U.S.C. 154(b) by 576 days.

(21) Appl. No.: 12/514,692

(22) PCT Filed: Dec. 4, 2007

(86) PCT No.: PCT/JP2007/073742
§ 371 (c)(1),
(2), (4) Date: May 13, 2009

(87) PCT Pub. No.: WO2008/069337
PCT Pub. Date: Jun. 12, 2008

(65) Prior Publication Data
US 2010/0049066 A1    Feb. 25, 2010

(30) Foreign Application Priority Data

Dec. 4, 2006   (JP) ................................. 2006-327379
May 28, 2007  (JP) ................................. 2007-140975

(51) Int. Cl.
*A61B 5/0402* (2006.01)

(52) U.S. Cl. ...................................................... 600/519

(58) Field of Classification Search .................. 600/513, 600/519, 520
See application file for complete search history.

(56) References Cited

U.S. PATENT DOCUMENTS 6,070,098 A    5/2000 Moore-Ede et al.
(Continued)

FOREIGN PATENT DOCUMENTS

JP    A-1-131648    5/1989
(Continued)

OTHER PUBLICATIONS

International Preliminary Report on Patentability for corresponding international application No. PCT/JP2007/073742; Jun. 18, 2009.

(Continued)

*Primary Examiner* — Scott Getzow
*Assistant Examiner* — Amanda Patton
(74) *Attorney, Agent, or Firm* — Oliff & Berridge, PLC

(57) ABSTRACT

A device for judging a degree of awakening and a method for judging a degree of awakening which can more reliably detect weak sleepiness of people in action. The device for judging a degree of awakening in accordance with the present invention comprises a heartbeat sensor for acquiring a heartbeat signal from a driver and an ECU for detecting sleepiness of the driver by processing the heartbeat signal. In the ECU, a heartbeat signal preprocessing section for acquiring a heartbeat period time series from the heartbeat signal, a feature amount extracting section for acquiring a heartbeat fluctuation low frequency component power from the heartbeat period time series, a sleepiness detecting section for judging whether sleepiness occurs in the driver or not according the heartbeat fluctuation low frequency component power, a stimulus timing setting section for setting a timing for imparting a stimulus for removing sleepiness to the driver according to the heartbeat fluctuation low frequency component power, and a sleepiness removing stimulus output section for imparting the stimulus to the driver at thus set timing.

24 Claims, 29 Drawing Sheets

U.S. PATENT DOCUMENTS

| | | |
|---|---|---|
| 7,206,631 B2 * | 4/2007 | Kawachi et al. ............ 600/519 |
| 2004/0243013 A1 | 12/2004 | Kawachi et al. |
| 2005/0148894 A1 | 7/2005 | Misczynski et al. |

FOREIGN PATENT DOCUMENTS

| | | |
|---|---|---|
| JP | A-4-348759 | 12/1992 |
| JP | A-6-270711 | 9/1994 |
| JP | A-7-231880 | 9/1995 |
| JP | B2-2505072 | 6/1996 |
| JP | A-8-299443 | 11/1996 |
| JP | B2-2570329 | 1/1997 |
| JP | A-11-314534 | 11/1999 |
| JP | 2001-198113 | 7/2001 |
| JP | 2006-130046 | 5/2006 |
| JP | A-2006-158733 | 6/2006 |
| JP | 2006-247055 | 9/2006 |
| JP | A-2007-6970 | 1/2007 |
| JP | A-2007-195886 | 8/2007 |
| JP | A-2007-229218 | 9/2007 |
| JP | A-2007-264785 | 10/2007 |

OTHER PUBLICATIONS

Jul. 2, 2012 Search Report issued in European Patent Application No. 07850316.6.

* cited by examiner

Fig.15

| SLEEPINESS LEVEL | Sens VALUE RANGE |
|---|---|
| D0 | $0 \leq Sens < 1$ |
| D1 | $1 \leq Sens < 2$ |
| D2 | $2 \leq Sens < 3$ |
| D3 | $3 \leq Sens < 4$ |
| D4 | $4 \leq Sens < 5$ |

Sens: SENSORY EVALUATION AVERAGE VALUE

Fig.23

| HEART RATE (RR INTERVAL) | HEARTBEAT FLUCTUATION LOW FREQUENCY COMPONENT | THRESHOLD SET VALUE |
|---|---|---|
| INCREASE OR DECREASE | INCREASE | D2A |
| | UNCHANGED/DECREASE | D2B |
| UNCHANGED | INCREASE | D2C |
| | UNCHANGED/DECREASE | D2D |

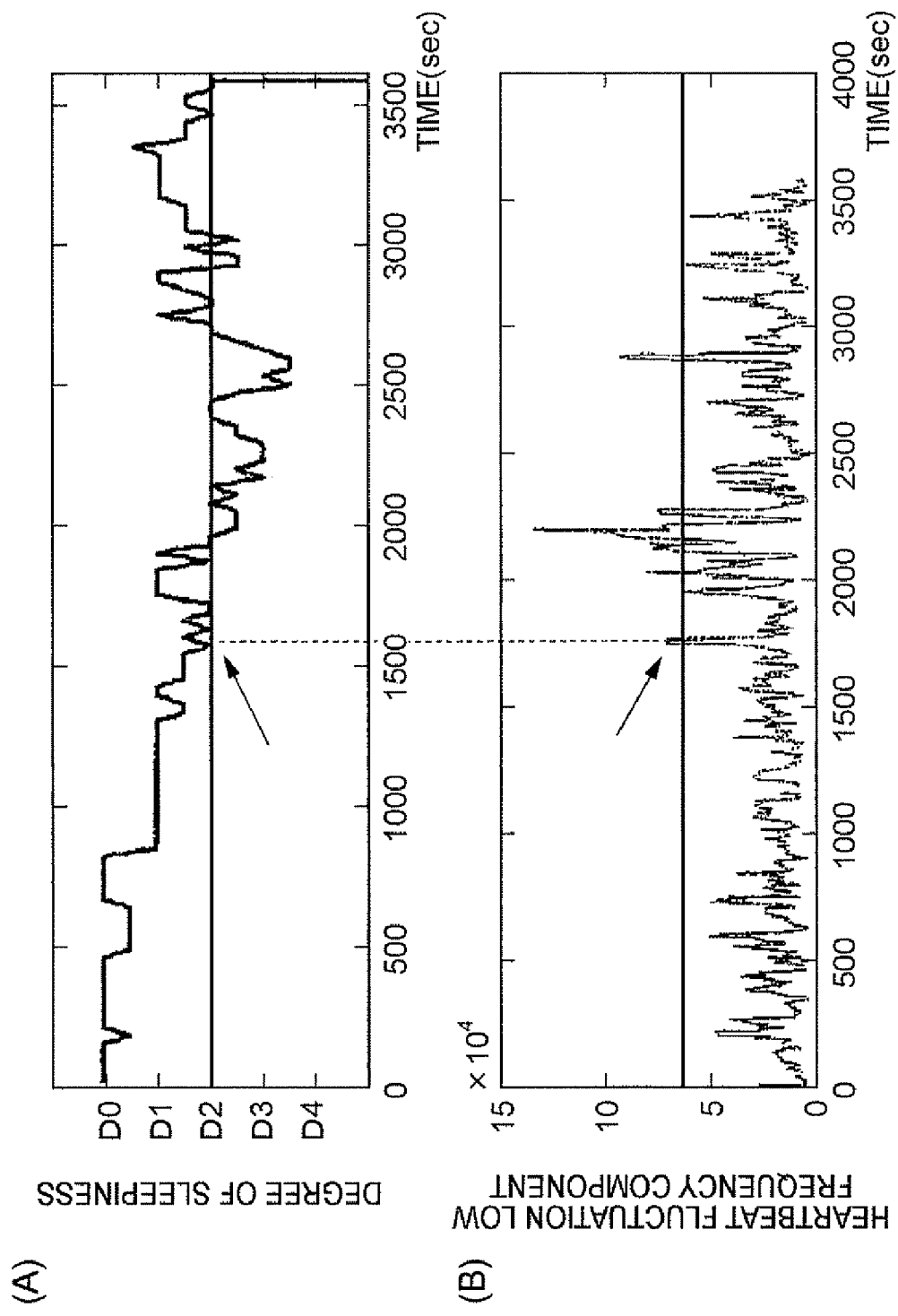

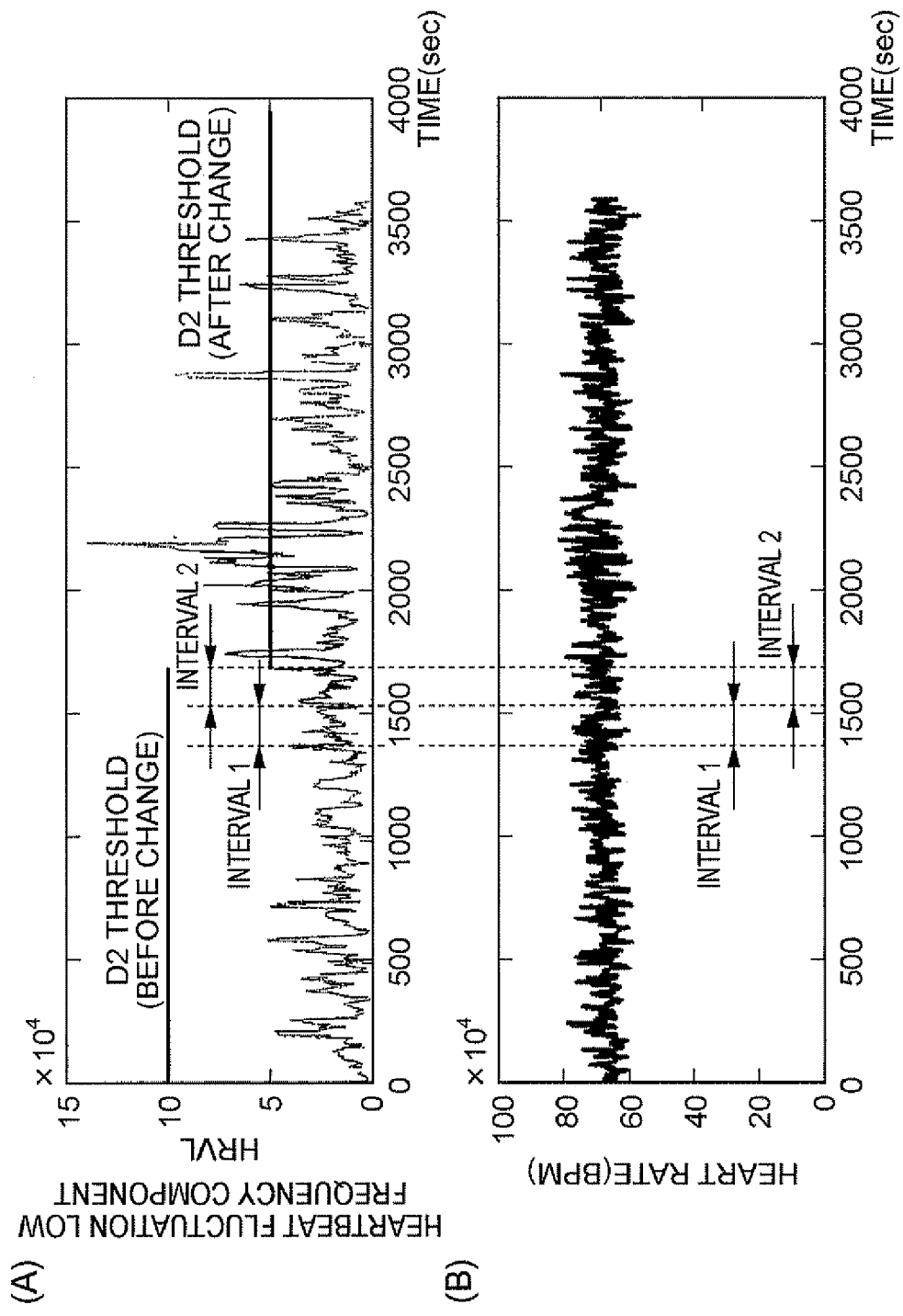

DEVICE FOR JUDGING DEGREE OF AWAKENING AND METHOD FOR JUDGING DEGREE OF AWAKENING

TECHNICAL FIELD

The present invention relates to a device for judging a degree of awakening and a method for judging a degree of awakening.

BACKGROUND ART

Techniques for detecting degrees of awakening of people have conventionally been proposed. As such a technique, Patent Document 1 discloses a technique which captures an image of an eyeball part of a person, extracts a pupil area of the eyeball part from the captured image, and judges that the degree of awakening is lowered when the time and frequency of blinks are found to be not less than predetermined values according to changes in the extracted shape of the pupil (Patent Document 1: Japanese Patent Application Laid-Open No. 6-270711).

DISCLOSURE OF THE INVENTION

Problem to be Solved by the Invention

However, the above-mentioned prior art judges the awakening state from the time and frequency of blinks and thus cannot detect the lowering of the degree of awakening unless it decreases so much (i.e., unless sleepiness is considerably strong). Therefore, techniques which can detect weak sleepiness of people in action have been in demand.

For overcoming the problem mentioned above, it is an object of the present invention to provide a device for judging a degree of awakening and a method for judging a degree of awakening which can more reliably detect weak sleepiness of people in action.

Means for Solving Problem

The device for judging a degree of awakening in accordance with the present invention comprises signal acquiring means for acquiring a biological signal of a person in action, index acquiring means for acquiring a physiological index indicating a strength of a state of acting against sleepiness from the biological signal acquired by the signal acquiring means, and judging means for judging the degree of awakening of the person according to the physiological index acquired by the index acquiring means.

The method for judging a degree of awakening in accordance with the present invention comprises a signal acquiring step of acquiring a biological signal of a person in action, an index acquiring step of acquiring a physiological index indicating a strength of a state of acting against sleepiness from the biological signal acquired by the signal acquiring step, and a judging step of judging the degree of awakening of the person according to the physiological index acquired by the index acquiring step.

Usually, the sleepiness of a person in action hinders the activity and thus is unfavorable. Therefore, even weak sleepiness causes a state in which a body acts against the sleepiness, i.e., a state in which the body battles against the sleepiness, thereby activating the body. The device or method for judging a degree of awakening in accordance with the present invention acquires a physiological index indicating a strength of a state of acting against sleepiness from a biological signal of a person in action and judges the degree of awakening according to the physiological index, thereby making it possible to detect weak sleepiness (lowering of the degree of awakening) of the person in action more reliably.

Preferably, as the physiological index, the device and method for judging a degree of awakening in accordance with the present invention use one correlated with a sympathetic activity.

As mentioned above, sleepiness during an activity is unfavorable. Therefore, the state of acting against sleepiness is a state where a stress acts on the person in action, thereby energizing the activity of the sympathetic nerve system. As the physiological index for judging the degree of awakening, one correlated with the sympathetic activity is used in the device or method for judging a degree of awakening in accordance with the present invention, whereby the state of the sympathetic nerve system, i.e., the state of acting against sleepiness, can be detected more reliably.

It will be preferred in particular if a heartbeat signal is used as the biological signal, and an amplitude spectral power of a heartbeat fluctuation low frequency component acquired from the heartbeat signal is used as the physiological index.

Since the amplitude spectral power of a heartbeat fluctuation low frequency component acquired from a heartbeat signal is correlated with the sympathetic activity, using the amplitude spectral power of a heartbeat fluctuation low frequency component as a physiological index for judging the degree of awakening can appropriately detect the state of the sympathetic activity, i.e., the state of acting against sleepiness.

Preferably, in the device for judging a degree of awakening in accordance with the present invention, the judging means judges that the degree of awakening is lowered when the amplitude spectral power of the heartbeat fluctuation low frequency component is greater than a predetermined value.

Preferably, in the method for judging a degree of awakening in accordance with the present invention, the judging step judges that the degree of awakening is lowered when the amplitude spectral power of the heartbeat fluctuation low frequency component is greater than a predetermined value.

As mentioned above, the amplitude spectral power of the heartbeat fluctuation low frequency component is correlated with the sympathetic activity, and its magnitude is correlated with the briskness of the sympathetic activity, i.e., the degree of acting against sleepiness. Therefore, as the degree of awakening decreases, so that the degree of acting against sleepiness becomes greater, the sympathetic activity becomes brisker, thereby increasing the amplitude spectral power of the heartbeat fluctuation low frequency component. The device or method for judging a degree of awakening in accordance with the present invention judges that the degree of awakening is lowered when the amplitude spectral power of the heartbeat fluctuation low frequency component is greater than a predetermined value, thereby making it possible to reliably detect a state where the degree of awakening is lowered while preventing erroneous detections from occurring.

Preferably, in the device for judging a degree of awakening in accordance with the present invention, the judging means judges that the degree of awakening is lowered more when the amplitude spectral power of the heartbeat fluctuation low frequency component is greater than when smaller.

Preferably, in the method for judging a degree of awakening in accordance with the present invention, the judging step judges that the degree of awakening is lowered more when the amplitude spectral power of the heartbeat fluctuation low frequency component is greater than when smaller.

As mentioned above, as the degree of awakening decreases, so that the degree of acting against sleepiness becomes greater, the sympathetic activity becomes brisker, thereby increasing the amplitude spectral power of the heartbeat fluctuation low frequency component. The device or method for judging a degree of awakening in accordance with the present invention judges that the degree of awakening is lowered more when the amplitude spectral power of the heartbeat fluctuation low frequency component is greater than when smaller, and thus can judge the magnitude of lowering in the degree of awakening.

Preferably, the device for judging a degree of awakening in accordance with the present invention further comprises stimulus providing means for imparting a stimulus for raising the degree of awakening to the person and timing setting means for setting a timing for providing the stimulus, while the timing setting means sets the timing for providing the stimulus according to the physiological index indicating the strength of the state of acting against the sleepiness.

Preferably, the method for judging a degree of awakening in accordance with the present invention further comprises a stimulus providing step of imparting a stimulus for raising the degree of awakening to the person and a timing setting step of setting a timing for providing the stimulus, while the timing setting step sets the timing for providing the stimulus according to the physiological index indicating the strength of the state of acting against the sleepiness.

Preferably, an appropriate timing for providing the stimulus for raising the degree of awakening coincides with or is slightly earlier than a timing when the person acting against sleepiness wants a stimulus. Here, the timing when the person acting against sleepiness wants a stimulus is correlated with the strength of the state of acting against sleepiness. The device or method for judging a degree of awakening in accordance with the present invention sets the timing for providing the stimulus for raising the degree of awakening according to the physiological index indicating the strength of the state of acting against sleepiness and thus can provide the stimulus at an appropriate timing.

Preferably, the device for judging a degree of awakening in accordance with the present invention further comprises stimulus providing means for imparting a stimulus for raising the degree of awakening to the person and timing setting means for setting a timing for providing the stimulus, while the timing setting means sets a timing for providing the stimulus before a predetermined time passes after the amplitude spectral power of the heartbeat fluctuation low frequency component exceeds a predetermined value.

Preferably, the method for judging a degree of awakening in accordance with the present invention further comprises a stimulus providing step of imparting a stimulus for raising the degree of awakening to the person and a timing setting step of setting a timing for providing the stimulus, while the timing setting step sets the timing for providing the stimulus before a predetermined time passes after the amplitude spectral power of the heartbeat fluctuation low frequency component exceeds a predetermined value.

In this case, the stimulus is provided before a predetermined time passes after the amplitude spectral power of the heartbeat fluctuation low frequency component exceeds a predetermined value, i.e., when the degree of awakening is lowered so that the degree of acting against sleepiness becomes greater, whereby the stimulus can be provided at an appropriate timing.

Preferably, the device for judging a degree of awakening in accordance with the present invention further comprises stimulus providing means for imparting a stimulus for raising the degree of awakening to the person and timing setting means for setting a timing for providing the stimulus, while the timing setting means sets the timing for providing the stimulus before the amplitude spectral power of the heartbeat fluctuation low frequency component attains the nearest local minimum after exceeding a predetermined value.

Preferably, the method for judging a degree of awakening in accordance with the present invention further comprises a stimulus providing step of imparting a stimulus for raising the degree of awakening to the person and a timing setting step of setting a timing for providing the stimulus, while the timing setting step sets the timing for providing the stimulus before the amplitude spectral power of the heartbeat fluctuation low frequency component attains the nearest local minimum after exceeding a predetermined value.

In this case, the stimulus is provided before the amplitude spectral power of the heartbeat fluctuation low frequency component attains the nearest local minimum after exceeding a predetermined value, i.e., during when the person in action acts against sleepiness, whereby the stimulus can be provided at an appropriate timing.

Preferably, as the physiological index, the device and method for judging a degree of awakening in accordance with the present invention use one correlated with a sympathetic activity and one correlated with a parasympathetic activity.

As mentioned above, the activity of the sympathetic nerve system is energized in the state of acting against sleepiness. Here, the activity of the parasympathetic nerve system usually decreases. However, there is an exceptional case where the activity of the parasympathetic nerve system increases together with the activity of the sympathetic nerve system. The device or method for judging a degree of awakening in accordance with the present invention takes account of the physiological index correlated with the parasympathetic activity in addition to the physiological index correlated with the sympathetic activity, and thus can accurately detect the state of truly acting against sleepiness while excluding the above-mentioned exceptional case.

It will be preferred in particular if a heartbeat signal is used as the biological signal, and respective amplitude spectral powers of heartbeat fluctuation high and low frequency components acquired from the heartbeat signal are used as the physiological index.

Since the amplitude spectral power of the heartbeat fluctuation high frequency component acquired from the heartbeat signal is correlated with the parasympathetic activity, further using the heartbeat fluctuation high frequency component as the physiological index can exclude the above-mentioned exceptional case.

Preferably, in the device for judging a degree of awakening in accordance with the present invention, the judging means judges whether the degree of awakening is lowered or not when the amplitude spectral power of the heartbeat fluctuation low frequency component is greater than the amplitude spectral power of the heartbeat fluctuation high frequency component.

Preferably, in the method for judging a degree of awakening in accordance with the present invention, the judging step judges whether the degree of awakening is lowered or not when the amplitude spectral power of the heartbeat fluctuation low frequency component is greater than the amplitude spectral power of the heartbeat fluctuation high frequency component.

In this case, whether or not the degree of awakening is lowered is determined when the amplitude spectral power of the heartbeat fluctuation low frequency component is greater than the amplitude spectral power of the heartbeat fluctuation high frequency component, whereby the above-mentioned exceptional case can appropriately be excluded. Therefore, only the state of truly acting against sleepiness can be detected.

Preferably, the device for judging a degree of awakening in accordance with the present invention further comprises threshold setting means for setting a threshold for judging whether the degree of awakening of the person is lowered or not, and the judging means judges that the degree of awakening of the person is lowered when the amplitude spectral power of the heartbeat fluctuation low frequency component is greater than the threshold.

Preferably, the method for judging a degree of awakening in accordance with the present invention further comprises a threshold setting step of setting a threshold for judging whether the degree of awakening of the person is lowered or not, and the judging step judges that the degree of awakening of the person is lowered when the amplitude spectral power of the heartbeat fluctuation low frequency component is greater than the threshold.

Preferably, the threshold for judging whether the degree of awakening of the person is lowered or not is changed according to individual differences, changes in physical conditions in the day even in the case of the same person, or the like, for example. In this case, the threshold setting means or threshold setting step sets the threshold. Then, when the amplitude spectral power of the heartbeat fluctuation low frequency component is greater than the threshold, it is judged that the degree of awakening is lowered. Hence, sleepiness can be detected according to characteristics of each person, whereby the accuracy in sleepiness detection can be improved.

Preferably, in the device for judging a degree of awakening in accordance with the present invention, the threshold setting means sets the threshold according to the heartbeat signal and the amplitude spectral power of the heartbeat fluctuation low frequency component.

Preferably, in the method for judging a degree of awakening in accordance with the present invention, the threshold setting step sets the threshold according to the heartbeat signal and the amplitude spectral power of the heartbeat fluctuation low frequency component.

When thus set according to the heartbeat signal and the amplitude spectral power of the heartbeat fluctuation low frequency component, the threshold can conform to physiological characteristics of each person.

EFFECT OF THE INVENTION

The present invention employs such a structure as to acquire a physiological index indicating a strength of a state of acting against sleepiness from a biological signal of a person in action and judge a degree of awakening according to the physiological index, whereby weak sleepiness of people in action can be detected more reliably.

BRIEF DESCRIPTION OF THE DRAWINGS

FIG. 15 is a table showing criteria for judging sensory evaluation levels (sleepiness levels);

FIG. 23 is a table showing relationships among the heart rate, low frequency component of a heartbeat fluctuation, and set thresholds;

FIG. 28 is a diagram showing sleepiness detection results obtained when the sleepiness judging threshold is made variable; and FIG. 29 is a diagram showing an example of results of changing the sleepiness judging threshold.

Figure 1:
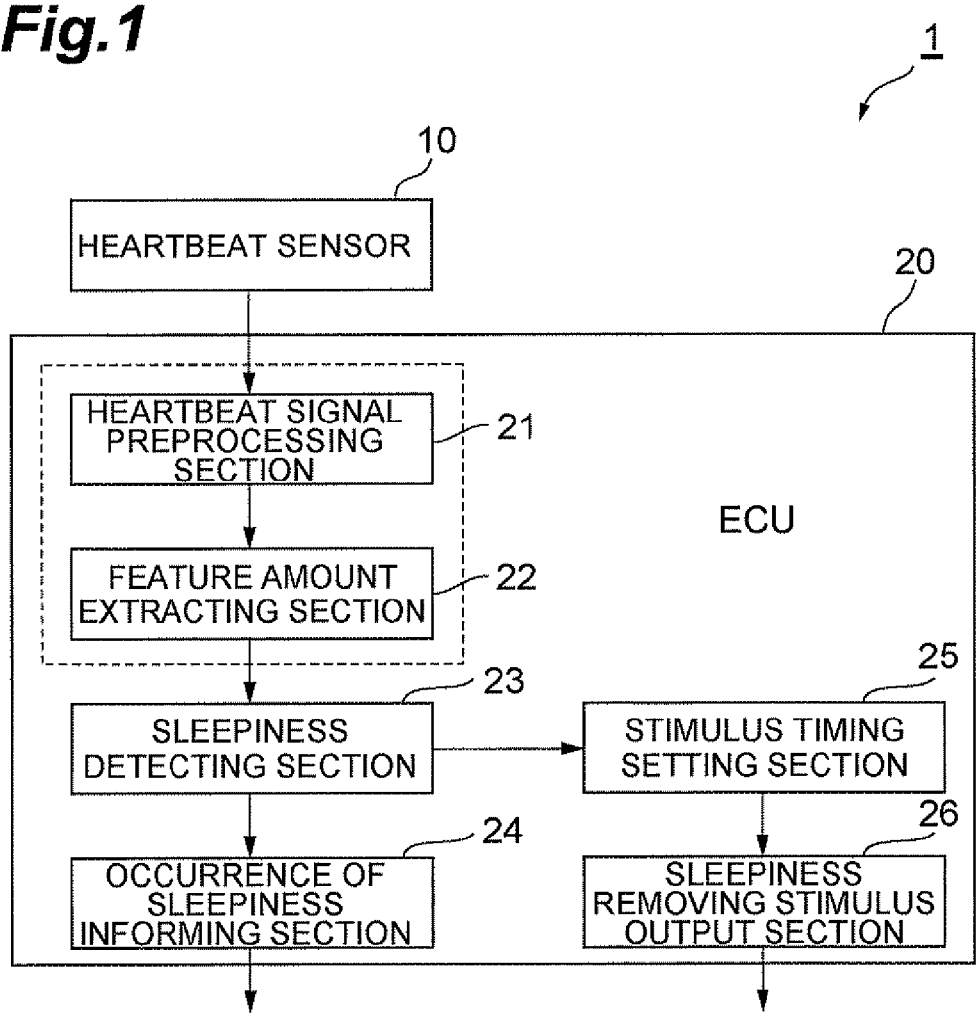
FIG. 1 is a block diagram showing an overall structure of the device for judging a degree of awakening in accordance with a first embodiment.

EXPLANATION OF NUMERALS 1, 2 . . . device for judging a degree of awakening; 10 . . . heartbeat sensor; 20, 20D . . . ECU; 21 . . . heartbeat signal preprocessing section; 22, 22D . . . feature amount extracting section; 23, 23D . . . sleepiness detecting section; 24 . . . occurrence of sleepiness informing section; 25 . . . stimulus timing setting section; 26 . . . sleepiness removing stimulus output section; 27 . . . threshold setting section

BEST MODES FOR CARRYING OUT THE INVENTION

In the following, preferred embodiments of the present invention will be explained in detail with reference to the drawings. In the drawings, the same or equivalent parts will be referred to with the same numerals.
[First Embodiment]

To begin with, an overall structure of the device for judging a degree of awakening 1 in accordance with the first embodiment will be explained with reference to FIG. 1. FIG. 1 is a block diagram showing the overall structure of the device 1. In the following, a case where the device 1 is mounted to a vehicle and detects lowering in the degree of awakening of a driver of the vehicle will be explained by way of example.

The device 1 is one which detects whether the driver's degree of awakening is lowered or not according to a heartbeat signal obtained from the driver, and presents the result of detection to the driver or provides a stimulus for raising the degree of awakening. For this purpose, the device 1 comprises a heartbeat sensor 10 and an electronic control unit (hereinafter referred to as "ECU") 20, while a heartbeat signal preprocessing section 21, a feature amount extracting section 22, a sleepiness detecting section 23, an occurrence of sleepiness informing section 24, a stimulus timing setting section 25, and a sleepiness removing stimulus output section 26 are constructed in the ECU 20.

The heartbeat sensor 10, which is a potentiometric heartbeat sensor for detecting a pulsed voltage (cardiac potential) occurring when cardiac muscle contracts, acquires a heartbeat signal of the driver. The heartbeat sensor 10 detects the cardiac potential from an electrode attached to a steering wheel of the vehicle or the like, for example. The heartbeat sensor 10 outputs the acquired heartbeat signal to the ECU 20. The heartbeat sensor 10 functions as the biological signal acquiring means recited in the claims and executes the biological signal acquiring step.

The ECU 20 is constituted by a microprocessor for performing arithmetic operations, a ROM storing programs and the like for causing the microprocessor to execute each processing, a RAM for storing various kinds of data such as results of the arithmetic operations, a backup RAM holding its stored contents with a battery, and the like.

The heartbeat signal preprocessing section 21 reads the heartbeat signal from the heartbeat sensor 10 at predetermined time intervals, so as to acquire a heartbeat period (RR interval) time series from the heartbeat signal. More specifically, after subjecting the heartbeat signal to a bandpass filtering processing, time series data exceeding a threshold is cut out. Subsequently, thus out-out time series data is binarized, and an interval width (period) is determined by utilizing the binarized data. Then, the interval width is interpolated, so as to determine time series data of the heartbeat period. The heartbeat period time series acquired by the heartbeat signal preprocessing section 21 is outputted to the feature amount extracting section 22.

From the heartbeat period time series acquired by the heartbeat signal preprocessing section 21, the feature amount extracting section 22 acquires an amplitude spectral power (time series) of a heartbeat fluctuation low frequency component which is a physiological index indicating a strength of a state of acting against sleepiness. More specifically, first, the heartbeat period time series data is subjected to FFT processing, so as to acquire an amplitude spectrum which is a heartbeat fluctuation frequency component. Subsequently, a frequency band of a low frequency component is designated for this amplitude spectrum, and the amplitude spectrum of this band is integrated. This processing is performed repeatedly, so as to acquire an amplitude spectral power time series of the heartbeat fluctuation low frequency component. Thus, the heartbeat signal preprocessing section 21 and the feature amount extracting section 22 function as the index acquiring means recited in the claims and execute the index acquiring step. The amplitude spectral power (time series) of the heartbeat fluctuation low frequency component acquired by the feature amount extracting section 22 is outputted to the sleepiness detecting section 23.

According to the amplitude spectral power (time series) of the heartbeat fluctuation low frequency component acquired by the feature amount extracting section 22, the sleepiness detecting section 23 judges whether or not sleepiness occurs in the driver (i.e., a degree of awakening of the driver). More specifically, when the amplitude spectral power of the heartbeat fluctuation low frequency component (hereinafter referred to as "heartbeat fluctuation low frequency component power") is not greater than a first sleepiness judging threshold $D1$, it is judged to be a state without sleepiness. When the heartbeat fluctuation low frequency component power is greater than the first sleepiness judging threshold $D1$ but not greater than a second sleepiness judging threshold $D2$, it is judged to be a state with weak sleepiness (state where the degree of awakening is lowered slightly). When the heartbeat fluctuation low frequency component power is greater than the second sleepiness judging threshold $D2$, it is judged to be a state with strong sleepiness (state where the degree of awakening is lowered greatly) (see FIG. 13). Here, the second sleepiness judging threshold $D2$>the first sleepiness judging threshold $D1$. Thus, the sleepiness detecting section 23 functions as the judging means recited in the claims and executes the judging step.

Methods for setting the first sleepiness judging threshold $D1$ and second sleepiness judging threshold $D2$ will now be explained. An example is a method which acquires a correlation between sleepiness, which is quantified by another method, and the heartbeat fluctuation low frequency component power. Known as a method for quantifying sleepiness is one which evaluates a sleepiness level from a face image (see "Human Sensory Measurement Manual, Vol. 1", p. 146, Research Institute of Human Engineering for Quality Life). The method for setting the first sleepiness judging threshold $D1$ and second sleepiness judging threshold $D2$ is not limited to this method; they may be set by learning in view of health conditions of the driver such as blood pressure and heart rate.

When weak sleepiness is detected by the sleepiness detecting section 23, a flag indicating a weak sleepiness state is outputted to the occurrence of sleepiness informing section 24. When strong sleepiness is detected by the sleepiness detecting section 23, on the other hand, this fact and the heartbeat fluctuation low frequency component power (time series) are outputted to the stimulus timing setting section 25.

The occurrence of sleepiness informing section 24 is one which presents awakening degree lowering information to the driver when the flag indicating the weak sleepiness state is fed from the sleepiness detecting section 23. The occurrence of sleepiness informing section 24 presents the awakening degree lowering information by using a display for showing character information and visual information, a speaker for reproducing sound information, and the like.

Figure 14:
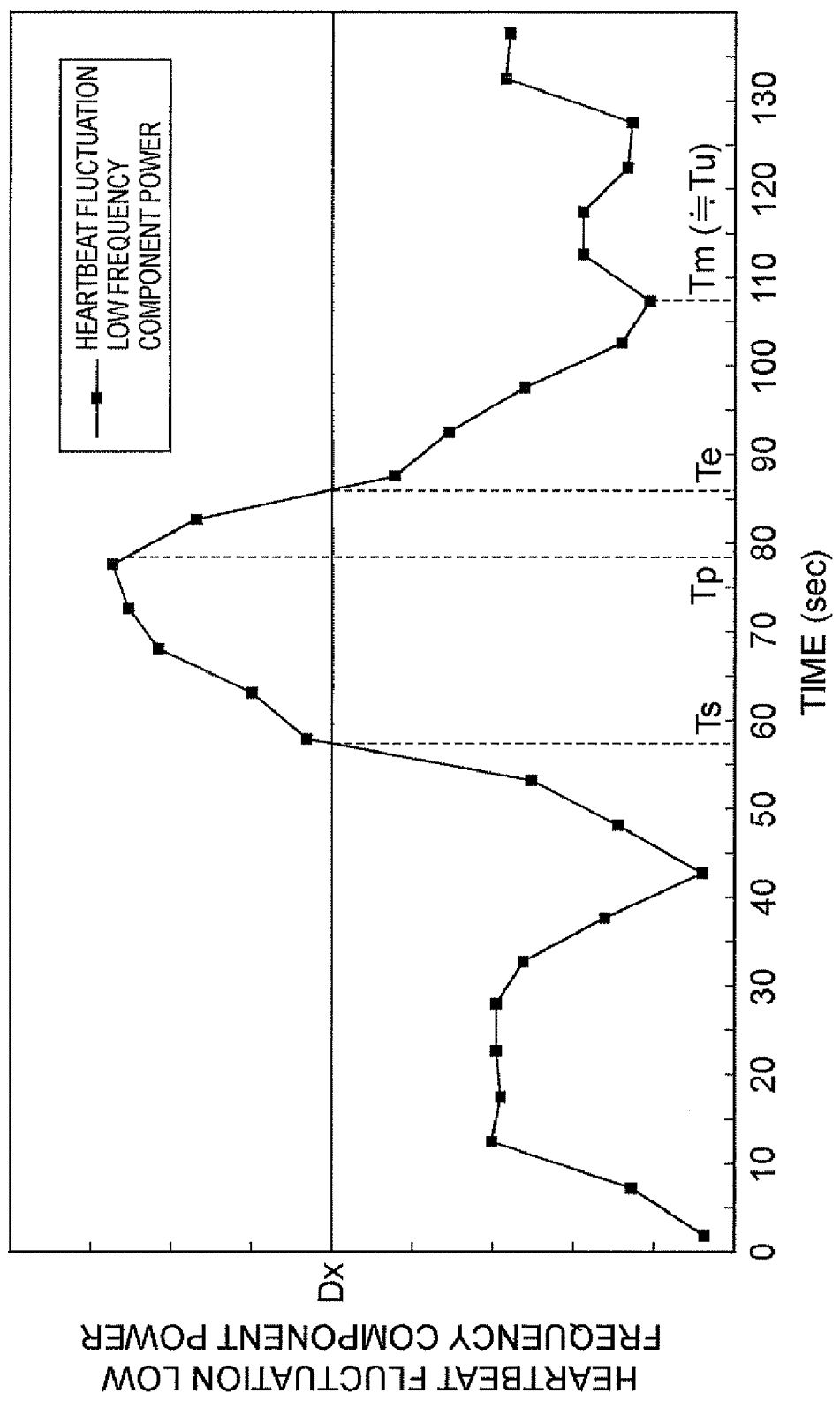
FIG. 14 is a diagram for explaining a method for setting a stimulus providing timing.

According to the heartbeat fluctuation low frequency component power (time series) fed from the sleepiness detecting section 23, the stimulus timing setting section 25 sets a timing for imparting a stimulus for removing sleepiness to the driver. More specifically, as shown in FIG. 14, the stimulus timing setting section 25 sets a timing for providing a stimulus before a predetermined time (e.g., 60 sec) passes from a time Ts when the heartbeat fluctuation low frequency component power exceeds a predetermined value Dx (the first sleepiness judging threshold D1 or second sleepiness judging threshold D2) or before the heartbeat fluctuation low frequency component power attains the nearest local minimum after exceeding the predetermined value (first sleepiness judging threshold D1 or second sleepiness judging threshold D2) (between times Ts and Tm). Hence, the stimulus timing setting section 25 functions as the timing setting means recited in the claims and executes the timing setting step. Also, the stimulus timing setting section 25 outputs a sleepiness removing stimulus signal to the sleepiness removing stimulus output section 26 at thus set timing.

The stimulus providing timing is thus set according to the following reason. It will be preferred if the timing for providing the stimulus coincides with or is slightly earlier than a timing at which a person acting against sleepiness wants a stimulus. Providing the stimulus at the timing when the driver wants a stimulus responds to the driver's demand and thus seems to be highly effective in removing sleepiness. The inventor conducted tests and, as a result, has found that the timing Tu at which the driver wants the stimulus is around the time Tm at which the heartbeat fluctuation low frequency component power attains the first local minimum after exceeding the predetermined value (first sleepiness judging threshold D1 or second sleepiness judging threshold D2) or within about 60 sec after the heartbeat fluctuation low frequency component power exceeds the predetermined value.

On the other hand, providing the stimulus slightly earlier than the timing at which the driver wants the stimulus seems to be highly effective in terms of suppressing sleepiness which may occur thereafter. However, the effectiveness seems to lower when the timing for providing the stimulus is too early. From these viewpoints, it will be preferred if the stimulus providing timing is between the time Ts when the heartbeat fluctuation low frequency component power exceeds the predetermined value and the time Te when the low frequency component power becomes lower than the predetermined value (i.e., during when the driver battles against sleepiness), or at a time Tp when the low frequency component power attains the local minimum (i.e., the sleepiness of the driver is the strongest).

As a result of totally considering the foregoing, the stimulus providing timing is set before the predetermined time (e.g., 60 sec) passes from the time Ts when the heartbeat fluctuation low frequency component power exceeds the predetermined value Dx (first sleepiness judging threshold D1 or second sleepiness judging threshold D2) or before the heartbeat fluctuation low frequency component power attains the nearest local minimum after exceeding the predetermined value (first sleepiness judging threshold D1 or second sleepiness judging threshold D2) (between the times Ts and Tm).

According to the sleepiness removing stimulus signal fed from the stimulus timing setting section 25, the sleepiness removing stimulus output section 26 imparts the stimulus for removing sleepiness to the driver. Examples of the stimulus imparted to the driver include the following stimuli: those by sounds using buzzers, audios, and horns; those by light using meter illumination and room illumination; those perceivable by tactile/thermal senses using vibrators embedded in the steering wheel or seat and air-conditioner winds; and those by scents using spraying of fragrances. The sleepiness removing stimulus output section 26 functions as the stimulus providing means recited in the claims and executes the stimulus providing step.

Figure 2:
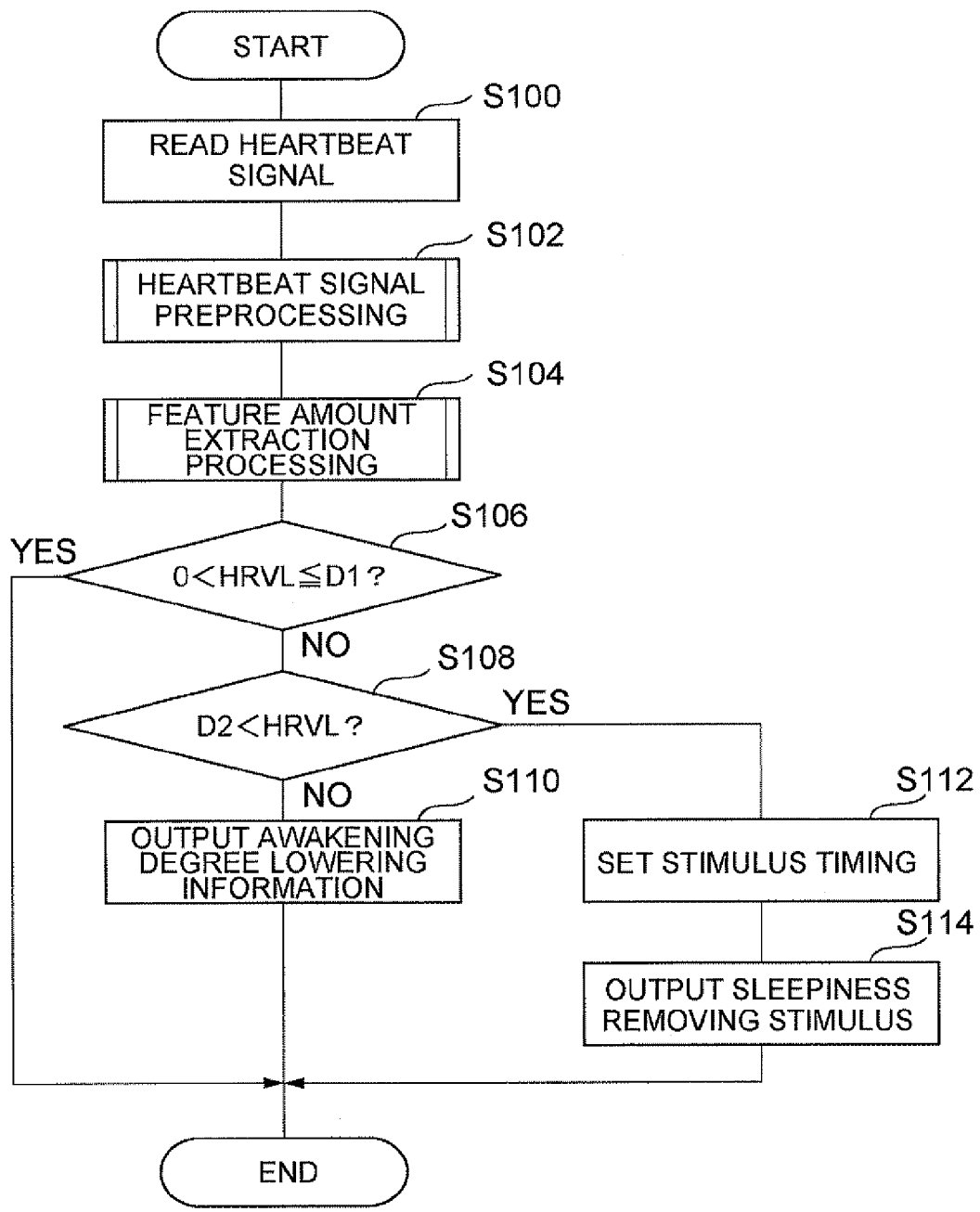
FIG. 2 is a flowchart showing a procedure of processing for detecting lowering of the degree of awakening by the device for judging a degree of awakening in accordance with the first embodiment.
Figure 3:
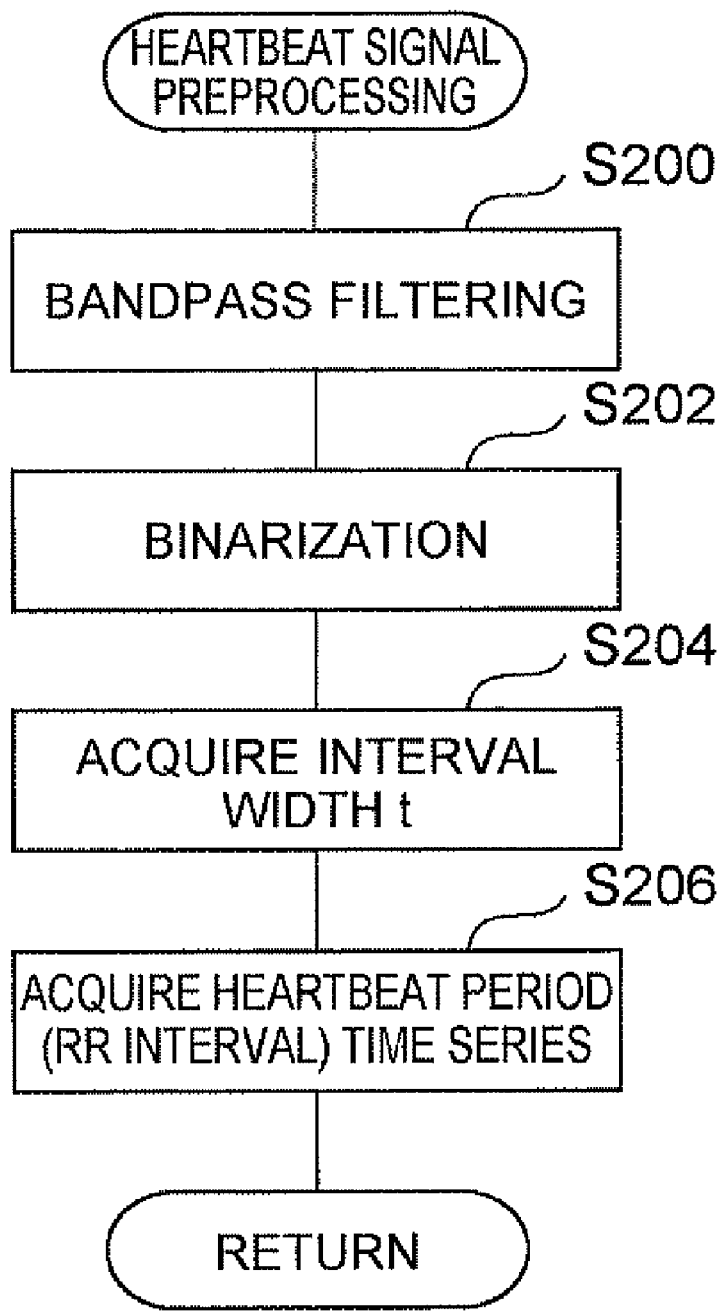
FIG. 3 is a flowchart showing a procedure of heartbeat signal preprocessing in the processing for detecting lowering of the degree of awakening.
Figure 4:
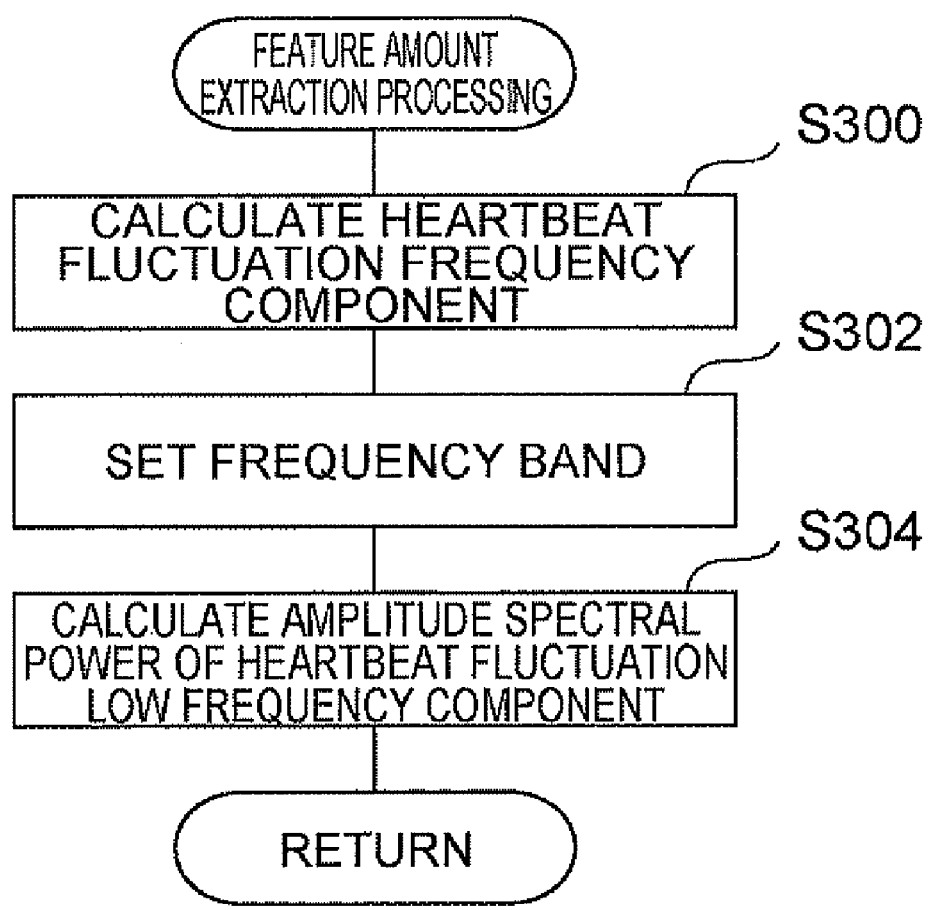
FIG. 4 is a flowchart showing a procedure of feature amount extraction processing in the processing for detecting lowering of the degree of awakening.

Using FIGS. 2 to 4 in combination with FIGS. 5 to 14, operations of the device for judging a degree of awakening 1 and the method for judging a degree of awakening will now be explained. FIG. 2 is a flowchart showing a procedure of processing for detecting lowering of the degree of awakening by the device for judging a degree of awakening 1. FIGS. 3 and 4 are flowcharts showing procedures of heartbeat signal preprocessing and feature amount extraction processing in the processing for detecting lowering of the degree of awakening. These kinds of processing, which are carried out by the ECU 20, are repeatedly executed at a predetermined timing before the power of the ECU 20 is turned off after being turned on.

At step S100, a heartbeat signal is read from the heartbeat sensor 10. At subsequent step S102, the heartbeat signal read at step S100 is preprocessed. The heartbeat signal preprocessing will now be explained with reference to FIG. 3.

Figure 5:
FIG. 5 is a diagram showing an example of heartbeat signals.

At step S200, heartbeat signal time series data is processed by a bandpass filter, whereby a passband component of 0.1 Hz to 30 Hz is extracted from the heartbeat signal time series data. FIG. 5 shows results of this processing.

Figure 6:
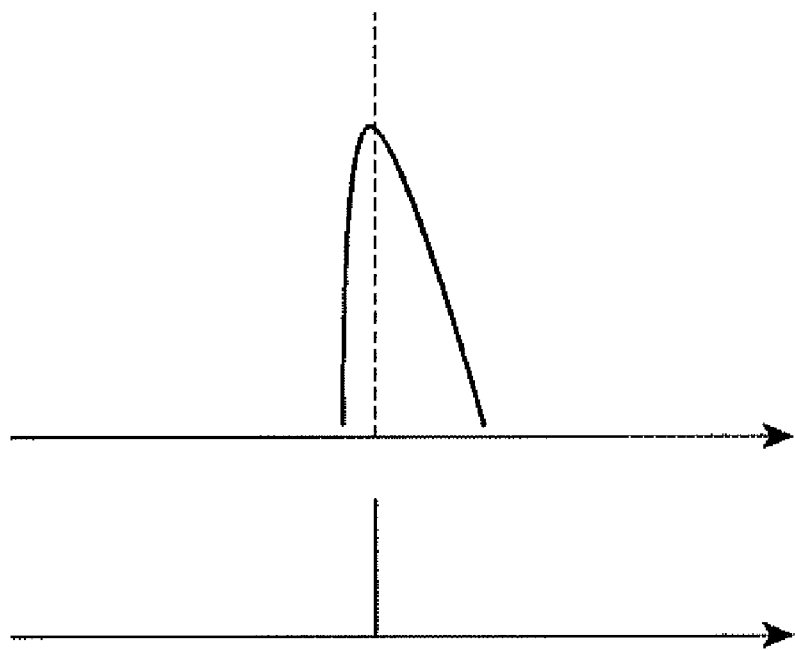
FIG. 6 is a schematic diagram for explaining binarization processing of the heartbeat signal.
Figure 7:
FIG. 7 is a schematic diagram showing a binary signal obtained by binarizing the heartbeat signal.

At step S202, as shown in FIG. 5, a wave portion not lower than a threshold $TH_0$ for detecting a heartbeat timing is cut out from the heartbeat signal time series data. Then, as shown in FIG. 6, the data is binarized such that timings at which the cut-out wave portion is maximized become 1 while the other timings become 0. Consequently, a series of heartbeat timings are determined as shown in FIG. 7.

Figure 8:
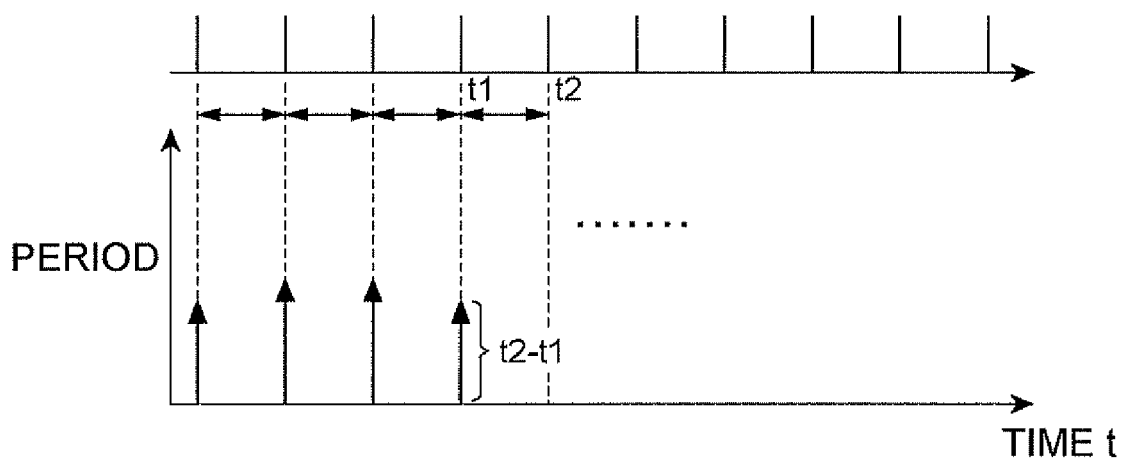
FIG. 8 is a schematic diagram for explaining processing for calculating a heartbeat period.

At subsequent step S204, as shown in FIG. 8, a time (sec) from each heartbeat timing t1 to the next heartbeat timing t2 is determined, and thus determined time (t2−t1) is imparted to each heartbeat timing t1, whereby heartbeat period information is obtained.

Figure 9:
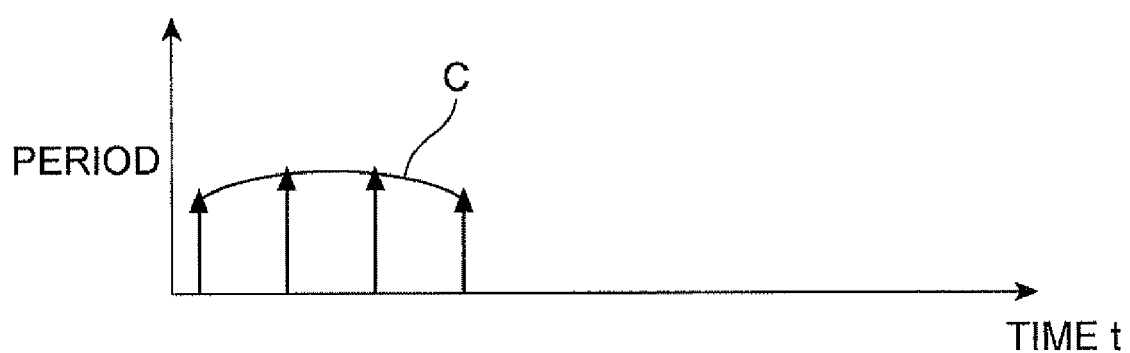
FIG. 9 is a schematic diagram for explaining interpolation processing for the heartbeat period.

At subsequent step S206, as shown in FIG. 9, the heartbeat period information is interpolated, so as to determine a heartbeat period curve C, thereby acquiring heartbeat period time series data. Thereafter, the processing shifts to step S104 shown in FIG. 2.

At step S104, feature amount extraction processing for acquiring a heartbeat fluctuation low frequency component power (time series) from the heartbeat period time series data acquired at step S206 is executed. The feature amount extraction processing will now be explained with reference to FIG. 4.

Figure 10:
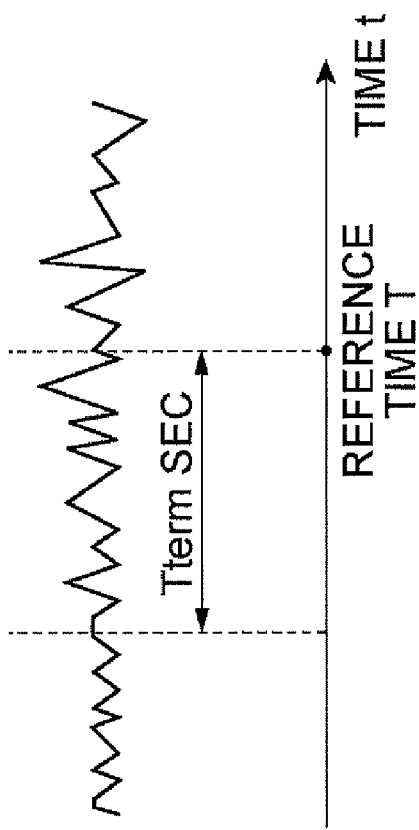
FIG. 10 is a schematic diagram for explaining FFT processing for the heartbeat period.

First, at step S300, the heartbeat period time series data in an analysis unit interval width Tterm (sec) prior to a reference time T which is a given timestamp is subjected to fast Fourier transform (FFT) processing as shown in FIG. 10.

Figure 11:
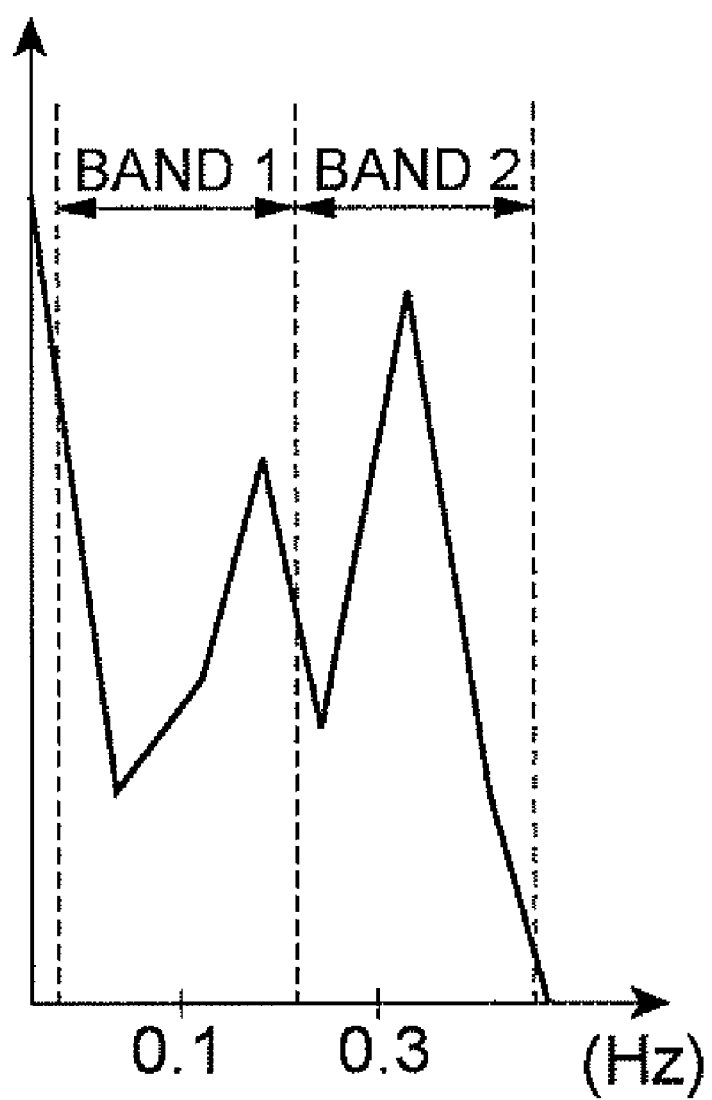
FIG. 11 is a schematic diagram for explaining integration of a power spectrum.

At subsequent step S302, as shown in FIG. 11, an amplitude spectrum is integrated in a frequency band of a low frequency component (around 0.1 Hz) in the power spectrum obtained for each analysis unit interval by the FET processing.

Figure 12:
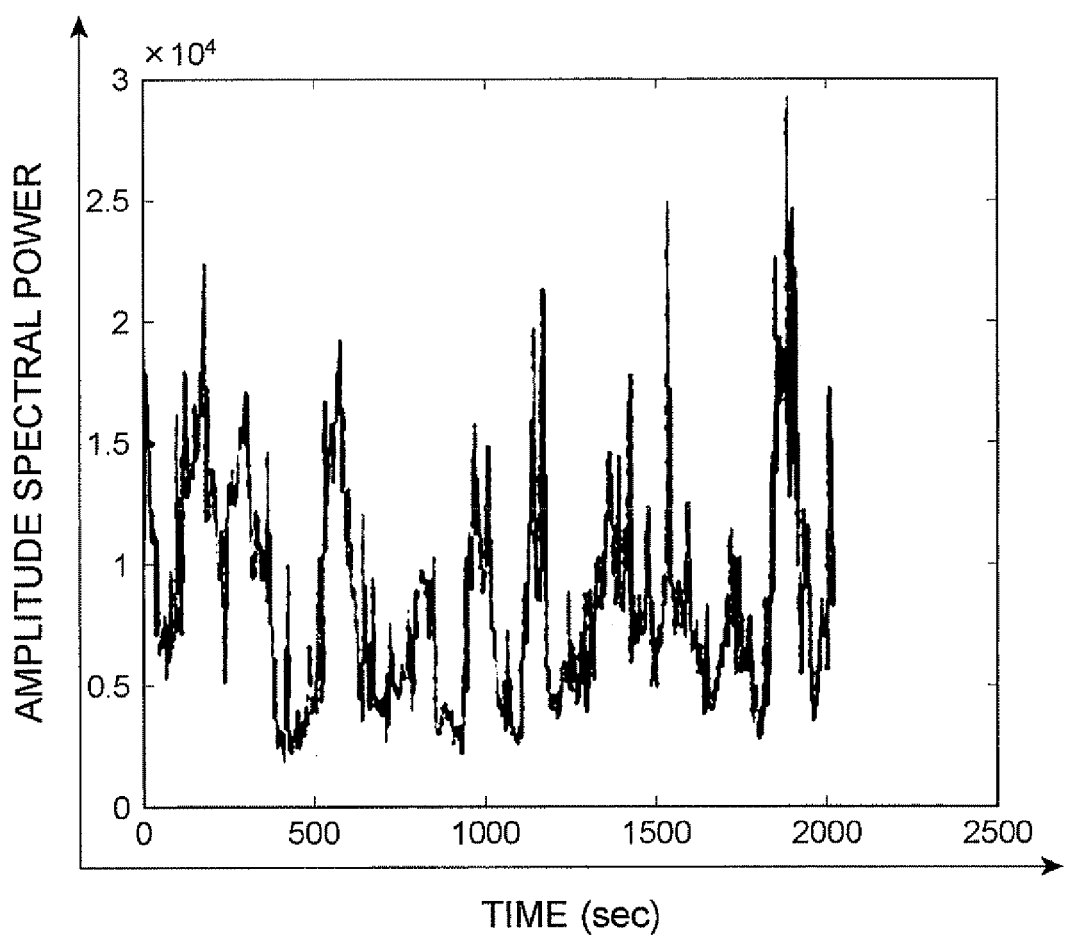
FIG. 12 is a chart showing changes in an amplitude spectral power with time.

At subsequent step S304, processing of subjecting the heartbeat period time series data in the analysis unit interval width Tterm to the FET processing and integrating the resulting power spectrum is repeated at each reference time after the lapse of a predetermined time. Consequently, as shown in FIG. 12, time series data of the amplitude spectral power in the frequency band of the lower frequency component is acquired. This time series data of the amplitude spectral power is a heartbeat fluctuation low frequency component power (time series). Thereafter, the processing shifts to step S106 shown in FIG. 2.

Figure 13:
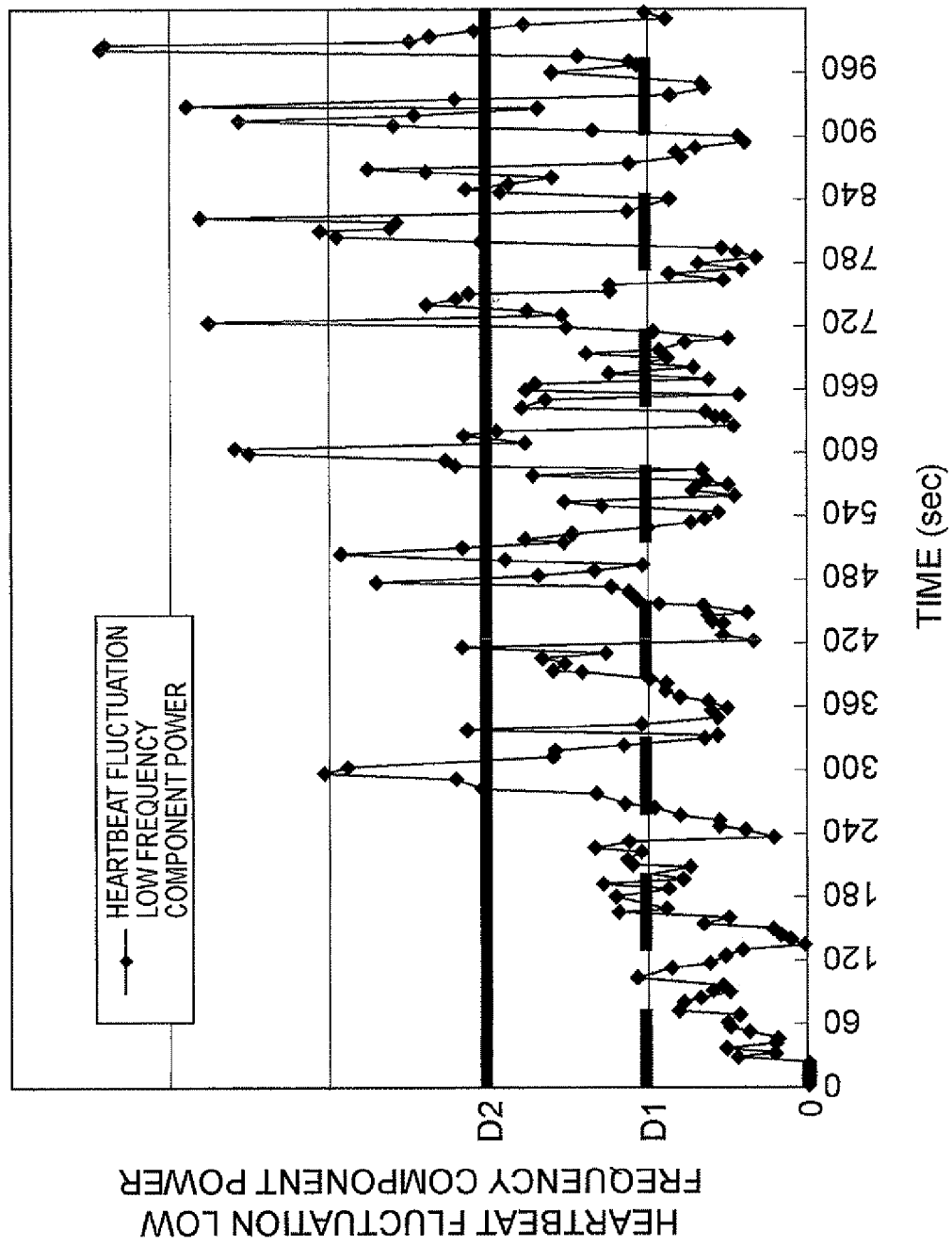
FIG. 13 is a diagram for explaining a method for detecting sleepiness (method for judging lowering of a degree of awakening)

At step S106, it is judged whether or not the heartbeat fluctuation low frequency component power is greater than 0 and not greater than the first sleepiness judging threshold D1 (see FIG. 13). When the heartbeat fluctuation low frequency component power is not greater than the first sleepiness judging threshold D1 here, it is judged to be a state without sleepiness, whereby this processing is once broken. When the heartbeat fluctuation low frequency component power is greater than the first sleepiness judging threshold D1, on the other hand, the processing shifts to step S108.

At step S108, it is judged whether the heartbeat fluctuation low frequency component power is greater than the second sleepiness judging threshold D2 or not (see FIG. 13). When the heartbeat fluctuation low frequency component power is not greater than the second sleepiness judging threshold D2 here, it is judged to be a state with weak sleepiness (state where the degree of awakening is lowered slightly), whereby the processing shifts to step S110. When the heartbeat fluctuation low frequency component power HRVL is greater than the second sleepiness judging threshold D2, on the other hand, it is judged to be a state with strong sleepiness (state where the degree of awakening is lowered greatly), whereby the processing shifts to step S112.

When it is judged to be the state with weak sleepiness, the awakening degree lowering information is presented to the driver at step S110. The awakening degree lowering information is presented by showing character information or visual information indicating that the degree of awakening is lowered or outputting sound information indicating that the degree of awakening is lowered from a speaker, for example. Thereafter, this processing is once broken.

When it is judged to be a state with strong sleepiness, on the other hand, a timing for imparting a stimulus for removing sleepiness to the driver is set at step S112 according to the heartbeat fluctuation low frequency component power (time series). More specifically, the stimulus providing timing is set before a predetermined time (e.g., 60 sec) passes from a time Ts when the heartbeat fluctuation low frequency component power exceeds the second sleepiness judging threshold D2. Alternatively, the stimulus providing timing is set before the heartbeat fluctuation low frequency component power attains the nearest local minimum after exceeding the second sleepiness judging threshold D2 (between times Ts and Tm) (see FIG. 14).

At subsequent step S114, a sleepiness removing stimulus signal is outputted according to the timing set at step S112, whereby the stimulus for removing sleepiness is imparted to the driver. For example, a stimulus by a sound using a buzzer, audio, or horn; a stimulus by light using meter illumination or room illumination; a stimulus perceivable by tactile/thermal senses using a vibrator embedded in the steering wheel or seat or an air-conditioner wind; a stimulus by a scent using spraying of a fragrance; or the like is imparted to the driver, so as to remove sleepiness.

Sleepiness of the driver when driving a vehicle hinders safe driving and thus is unfavorable. Therefore, even weak sleepiness causes a state in which the body acts against the sleepiness, i.e., a state in which the body battles against the sleepiness, thereby activating the body. This embodiment acquires a heartbeat fluctuation low frequency component power, which is a physiological index indicating a strength of a state of acting against sleepiness, from a heartbeat signal of the driver and judges the degree of awakening from the heartbeat fluctuation low frequency component power, thereby making it possible to more reliably detect weak sleepiness (lowering of the degree of awakening) of the driver during driving.

As mentioned above, sleepiness during driving is unfavorable, and the state of battling against sleepiness is a state where a stress acts on the driver. Therefore, the activity of the sympathetic nerve system of the driver is energized in such a state. As the physiological index for judging the degree of awakening, the heartbeat fluctuation low frequency component power correlated with the sympathetic activity is used in this embodiment, whereby the state of the sympathetic activity, i.e., the state of battling against sleepiness, can be detected more reliably.

As mentioned above, the heartbeat fluctuation low frequency component power is correlated with the sympathetic activity, and its magnitude is correlated with the briskness of the sympathetic activity, i.e., the degree of acting against sleepiness. Therefore, as the degree of awakening decreases, so that the degree of acting against sleepiness becomes greater, the sympathetic nerve becomes brisker, thereby increasing the heartbeat fluctuation low frequency component power. This embodiment judges that the degree of awakening is lowered when the heartbeat fluctuation low frequency component power is greater than the first sleepiness judging threshold D1, thereby making it possible to reliably detect a state where the degree of awakening is lowered while preventing erroneous detections from occurring.

As mentioned above, as the degree of awakening decreases, so that the degree of acting against sleepiness becomes greater, the sympathetic nerve becomes brisker, thereby increasing the heartbeat fluctuation low frequency component power. This embodiment judges that the degree of awakening is lowered more (sleepiness is stronger) when the heartbeat fluctuation low frequency component power is greater than the second sleepiness judging threshold D2, thereby making it possible to judge the strength of sleepiness.

This embodiment can detect lowering of the degree of awakening of the driver in an early stage, thereby making it possible to evade drowsy driving.

Preferably, an appropriate timing for providing the stimulus for removing sleepiness coincides with or is slightly earlier than a timing when the driver battling against sleepiness wants a stimulus. Here, the timing when the driver battling against sleepiness wants a stimulus is correlated with the strength of the state of acting against sleepiness. This embodiment sets the timing for providing the stimulus according to the heartbeat fluctuation low frequency component power, which is a physiological index indicating the strength of the state of acting against sleepiness, and thus can provide the stimulus at an appropriate timing.

This embodiment provides the stimulus before a predetermined time (e.g., 60 sec) passes after the heartbeat fluctuation low frequency component power exceeds the second sleepiness judging threshold D2, i.e., when the degree of awakening is lowered so that the degree of acting against sleepiness becomes greater, whereby the stimulus can be provided at an appropriate timing.

Also, this embodiment provides the stimulus before the heartbeat fluctuation low frequency component power attains the nearest local minimum after exceeding the second sleepiness judging threshold D2, i.e., when the driver battles against sleepiness (acts against sleepiness), whereby the stimulus can be provided at an appropriate timing.

EXAMPLE 1

As a functional evaluation test of the above-mentioned device for judging a degree of awakening 1, a test for detecting lowering of awakening was carried out. Here, results of sleepiness detection based on the heartbeat fluctuation low frequency component power of a subject (driver) and results of sleepiness level sensory evaluations obtained from face images were compared with each other, so as to perform the evaluation test. The method and results of the test will be explained. The test was carried out in the following procedure:

1. Acquire a face image time series of the subject simultaneously with measurement of a heartbeat signal.
2. Evaluate the face image time series with reference to the following levels 1 to 5 and classify the sleepiness of the subject into 5-stage levels (sensory evaluation). Here, the sensory evaluation was performed by two evaluators.
   Level 1: Not sleepy at all (the line of sight moves fast and frequently; blinking has a stable period of about 2 per 2 sec; movement is brisk with body actions).
   Level 2: Somewhat sleepy (lips are open; the line of sight moves slowly).
   Level 3: Sleepy (blinking is slowly and frequently; mouth moves; reseating; touching the face with a hand)
   Level 4: Fairly sleepy (there seems to be intentional blinking; unnecessary whole body actions such as shaking the head and moving the shoulder up and down; frequent yawning; deep breathing; blinking and movement of line of sight are slow)
   Level 5: Very sleepy (eyelids are closed; the head tilts forward; the head falls backward)
(ref: "Human Sensory Measurement Manual, Vol. 1", p. 146, Research Institute of Human Engineering for Quality Life)
3. Compute an average value Sens of functional evaluations by the two evaluators.
4. Acquire sleepiness levels D0 to D4 based on the sensory evaluation from the functional evaluation average value Sens according to the table shown in FIG. 15.
5. Simultaneously detect sleepiness of the subject by the device for judging a degree of awakening 1 according to the heartbeat fluctuation low frequency component power. For fairness of evaluation, the evaluators had not been provided with information about the heartbeat fluctuation low frequency component power acquired from the heartbeat signal of the subject at all.

Figure 16:
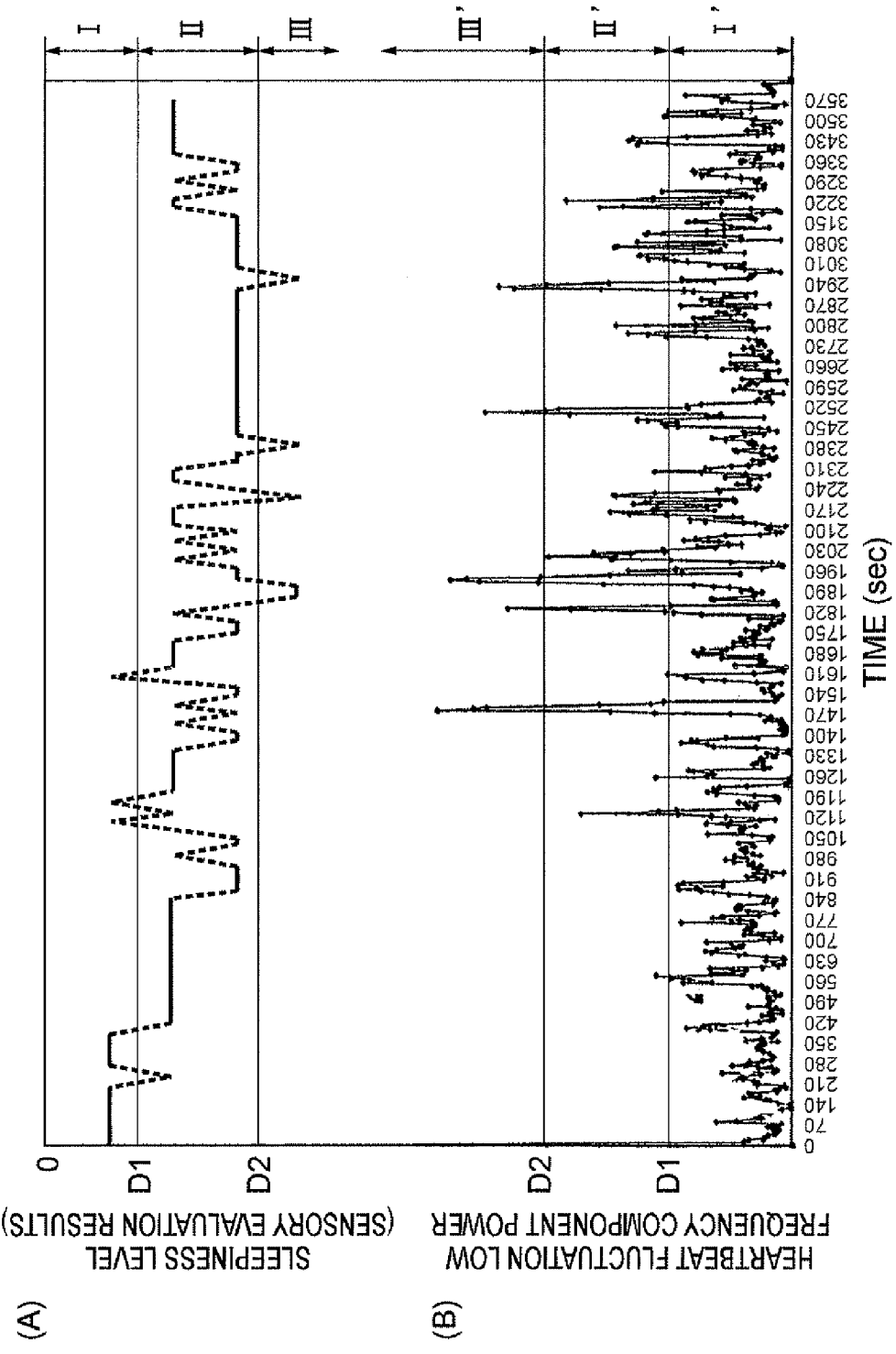
FIG. 16 is a diagram showing an example of sleepiness detection results.

FIG. 16 shows the results of the test for detecting lowering of the degree of awakening. In FIG. 16, while the abscissa indicates the lapse of time (sec), the upper part (A) shows the sleepiness level by the sensory evaluation, and the lower part (B) shows the results of sleepiness detection by the device for judging a degree of awakening 1 according to the heartbeat fluctuation low frequency component power. More specifically, areas I, II, and III in FIG. 16 are those judged by the sensory evaluation to be no sleepiness, somewhat sleepy, and sleepy, respectively. On the other hand, areas I', II', and III' in FIG. 16 are areas judged by the device for judging a degree of awakening 1 to be those with no sleepiness (0<heartbeat fluctuation low frequency component power≦first sleepiness judging threshold D1), weak sleepiness (first sleepiness judging threshold D1<heartbeat fluctuation low frequency component power≦second sleepiness judging threshold D2), and strong weakness (heartbeat fluctuation low frequency component power>second sleepiness judging threshold D2), respectively.

In the test results, when the sleepiness level by the sensory evaluation is level D1 (somewhat sleepy), it is judged to be weak sleepiness by the device for judging a degree of awakening 1. When the sleepiness level by the sensory evaluation is level D2 (sleepy), it is judged to be strong sleepiness by the device 1. Hence, the device 1 succeeded in detecting sleepiness of the subject, whereby the effectiveness of the device 1 has been verified.

EXAMPLE 2

A test for detecting lowering of awakening was carried out for a subject different from that of Example 1. The test method is the same as that of Example 1 mentioned above and thus will not be explained here.

Figure 17:
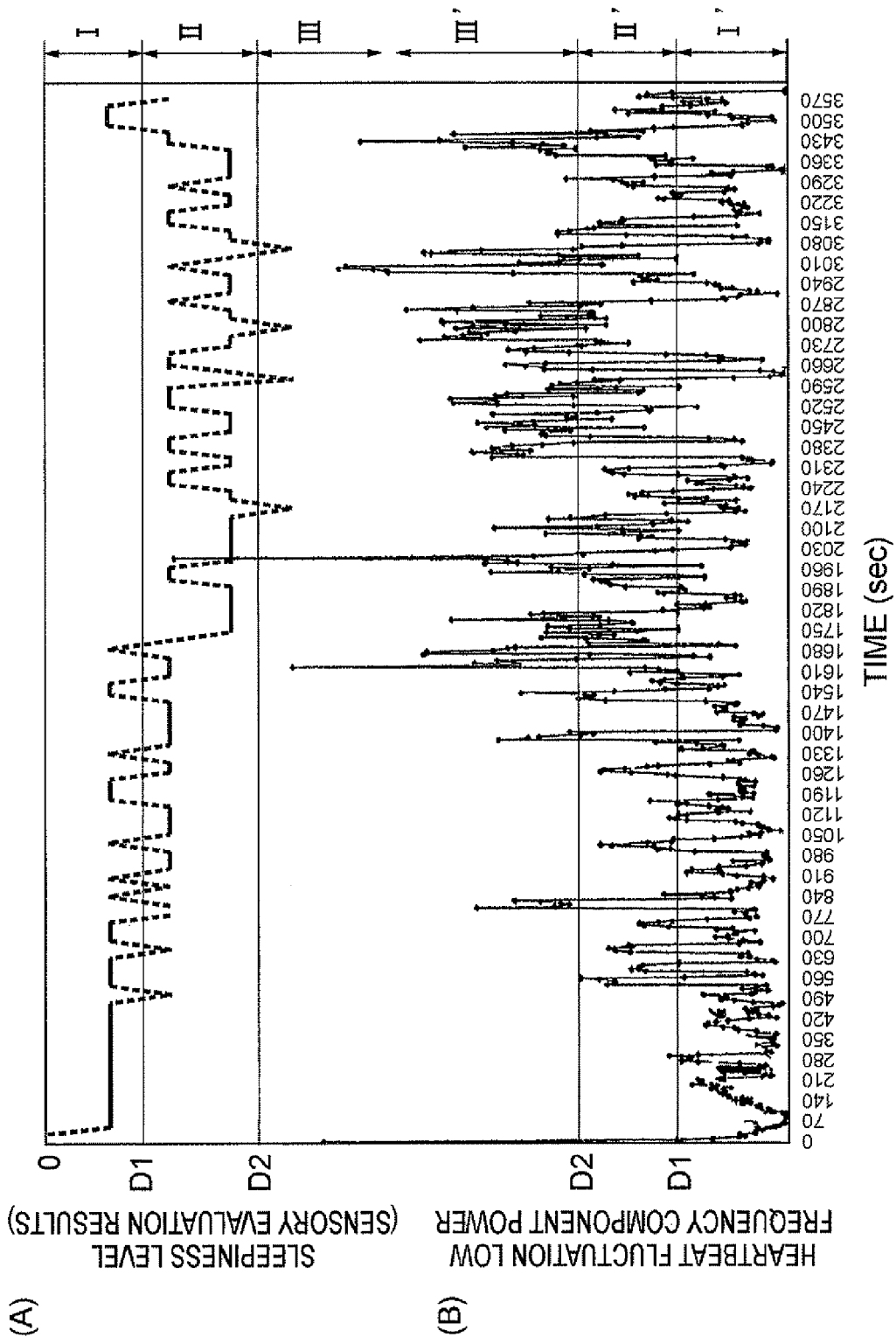
FIG. 17 is a diagram showing another example of sleepiness detection results.

FIG. 17 shows the results of the test for detecting lowering of the degree of awakening. When the sleepiness level by the sensory evaluation is level D1 (somewhat sleepy), it is judged to be weak sleepiness by the device for judging a degree of awakening 1 in these results of the test as well. When the sleepiness level by the sensory evaluation is level D2 (sleepy), it is judged to be strong sleepiness by the device 1. Hence, the device 1 succeeded in detecting sleepiness of the subject, whereby the effectiveness of the device 1 has been verified.

EXAMPLE 3

Figure 18:
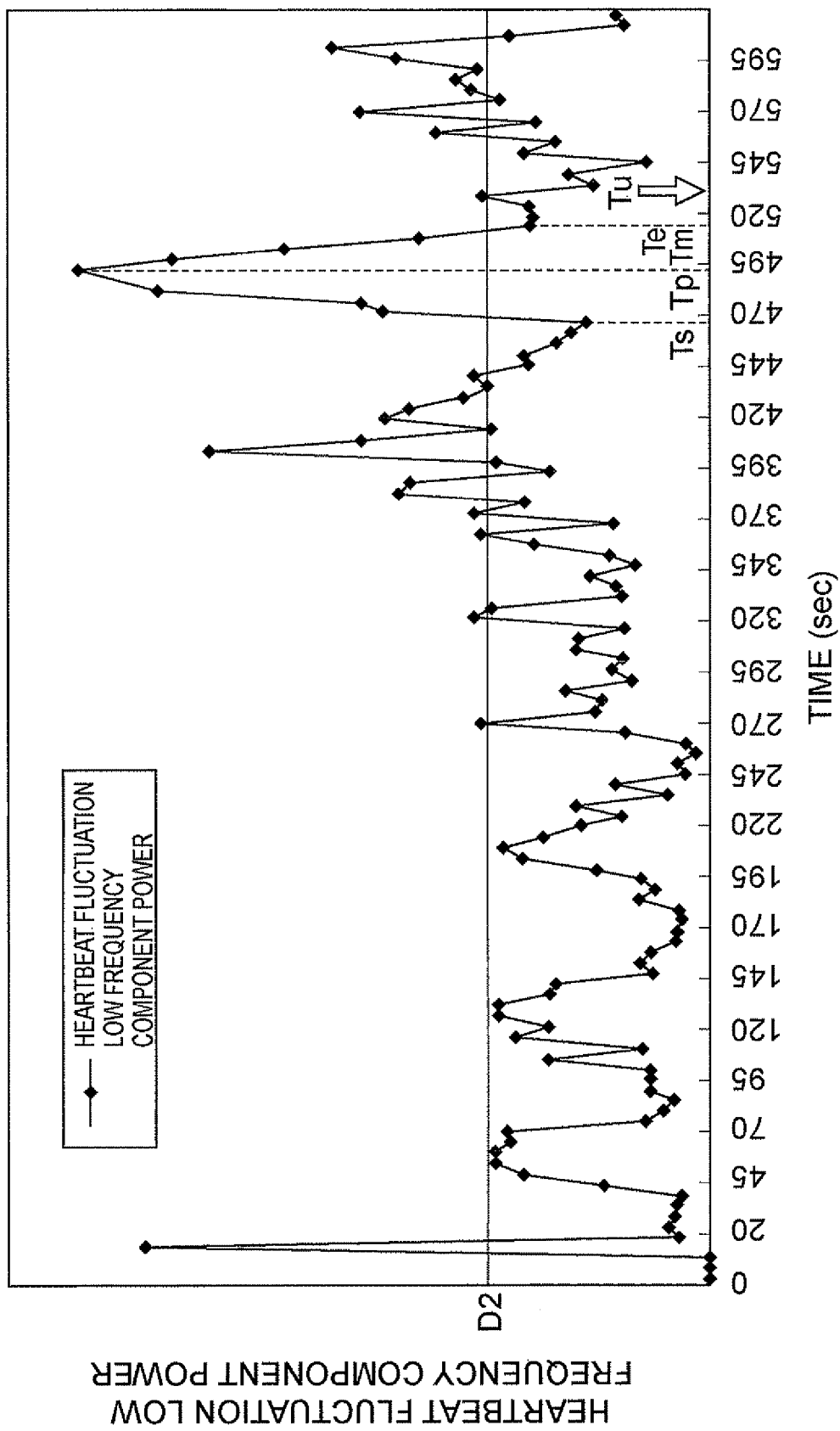
FIG. 18 is a diagram showing an example of stimulus providing timings.

As a test for evaluating the stimulus providing timing of the above-mentioned device for judging a degree of awakening 1, a stimulus providing timing test was carried out. Here, simultaneously with measurement of a heartbeat signal, a subject (driver) was asked to push a switch when feeling like wanting a stimulus for removing sleepiness. FIG. 18 shows the results of the stimulus providing timing test. The abscissa of FIG. 18 indicates the lapse of time (sec), while the ordinate indicates the heartbeat fluctuation low frequency component power. An arrow shows a timing at which the subject wants the stimulus.

In the test results, the timing at which the subject wanted the stimulus occurred before a predetermined time (60 sec) passed after the heartbeat fluctuation low frequency component power exceeded the second sleepiness judging threshold D2, whereby it has been verified that the stimulus providing timing set by the device for judging a degree of awakening 1 is appropriate.

EXAMPLE 4

A stimulus providing test was carried out for a subject different from that of Example 3. The test method is the same as that of Example 3 mentioned above and thus will not be explained here.

Figure 19:
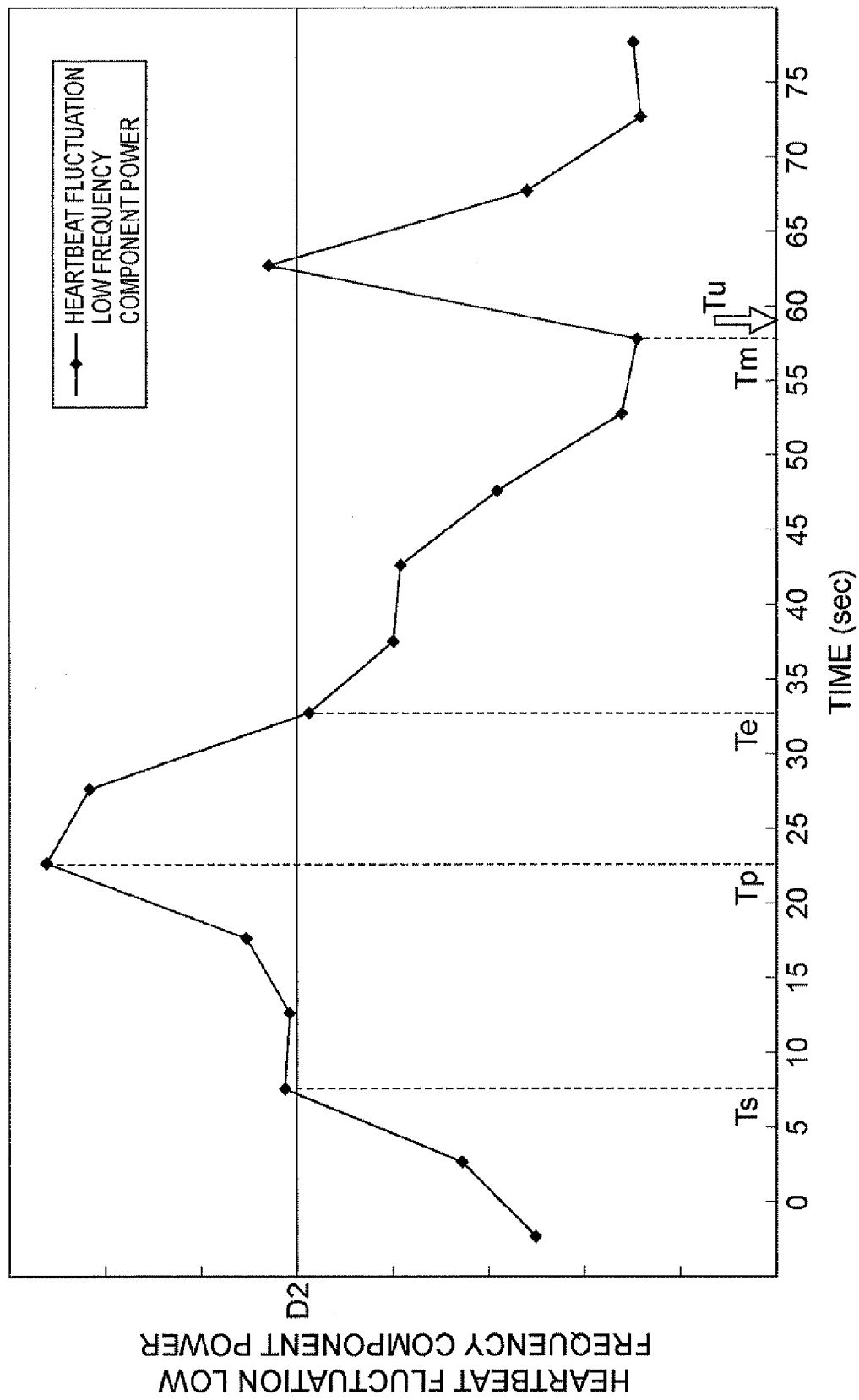
FIG. 19 is a diagram showing another example of stimulus providing timings.

FIG. 19 shows the results of the stimulus providing timing test. In this test, the timing at which the subject wanted the stimulus (see an arrow in FIG. 19) occurred before a predetermined time (60 sec) passed after the heartbeat fluctuation low frequency component power exceeded the second sleepiness judging threshold D2 and before the heartbeat fluctuation low frequency component power attained the nearest local minimum value after exceeding the second sleepiness judging threshold D2, whereby it has been verified that the stimulus providing timing set by the device for judging a degree of awakening 1 is appropriate.

[Second Embodiment]

Figure 20:
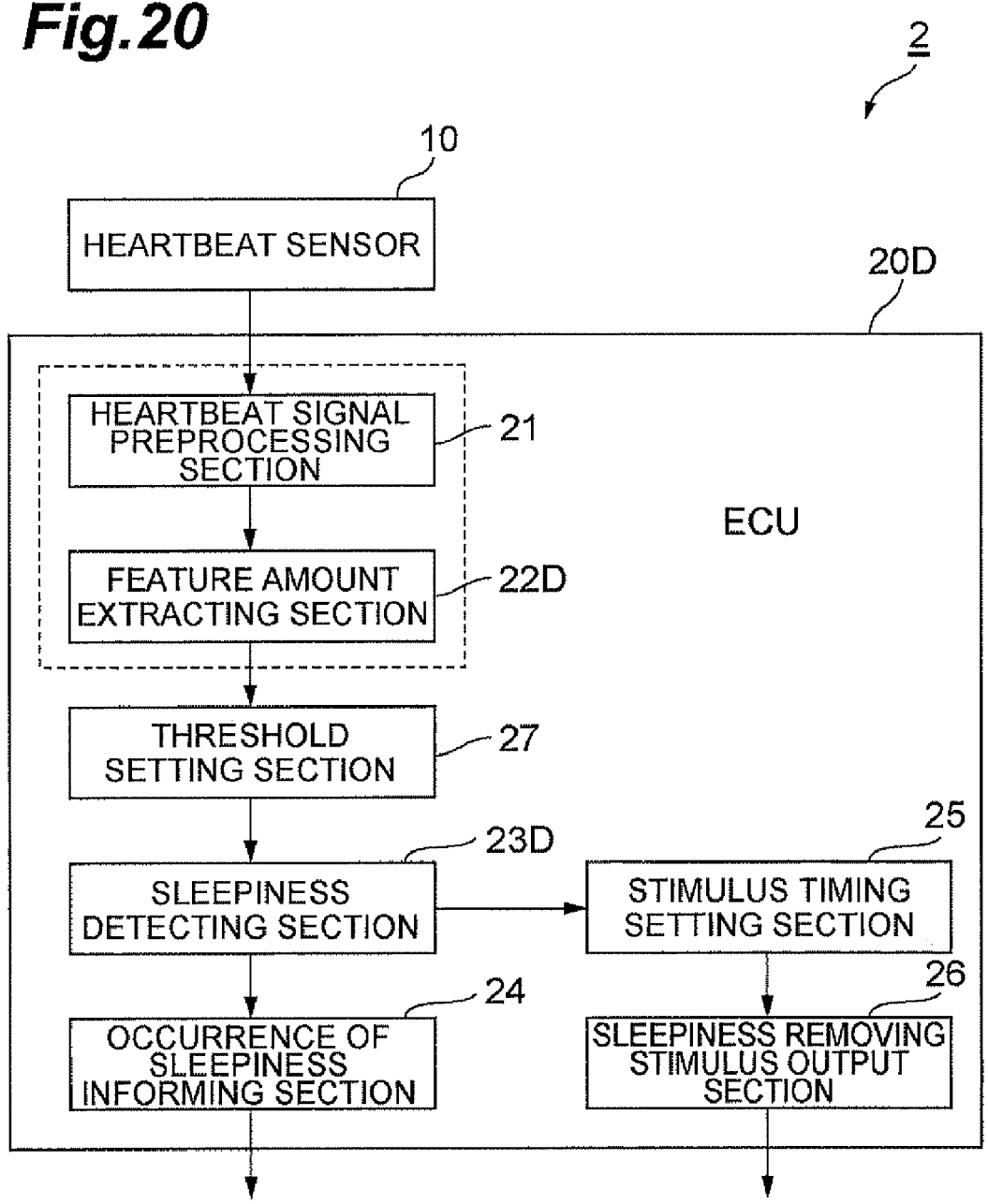
FIG. 20 is a block diagram showing an overall structure of the device for judging a degree of awakening in accordance with a second embodiment.

An overall structure of the device for judging a degree of awakening 2 in accordance with the second embodiment will be explained with reference to FIG. 20. FIG. 20 is a block diagram showing the overall structure of the device 2. In FIG. 20, constituents identical or equivalent to those in the first embodiment will be referred to with the same numerals or letters.

The device for judging a degree of awakening 2 differs from the first embodiment in that it is equipped with an ECU 20D instead of the above-mentioned ECU 20. More specifically, the ECU 20D differs from the ECU 20 in that it includes a feature amount extracting section 22D and a sleepiness detecting section 23D instead of the feature amount extracting section 22 and sleepiness detecting section 23 constituting the ECU 20. The ECU 20D also differs from the ECU 20 in that it further comprises a threshold setting section 27 for setting a threshold for judging whether or not sleepiness occurs in the driver. The structures of the remaining constituents are identical or similar to those of the above-mentioned first embodiment and thus will not be explained here.

The feature amount extracting section 22D differs from the feature amount extracting section 22 in that it acquires a spectral power (time series) of a heartbeat fluctuation high frequency component in addition to the heartbeat fluctuation low frequency component power (time series) from the heartbeat period time series acquired by the heartbeat signal preprocessing section 21. More specifically, first, the feature amount extracting section 22D subjects the time series data of the heartbeat period to FFT processing, so as to acquire an amplitude spectrum which is a heartbeat fluctuation frequency component. Subsequently, a frequency band of a high frequency component is designated for this amplitude spectrum, and the amplitude spectrum of this band is integrated. This processing is performed repeatedly, so as to acquire an amplitude spectral power time series of the heartbeat fluctuation high frequency component. The method for acquiring the heartbeat fluctuation low frequency component power time series is the same as that mentioned above and thus will not be explained here.

Thus, the heartbeat signal preprocessing section 21 and the feature amount extracting section 22D also function as the index acquiring means recited in the claims and execute the index acquiring step. The heartbeat fluctuation low frequency component power acquired by the feature amount extracting section 22D is outputted to the threshold setting section 27. The heartbeat fluctuation low frequency component power (time series) and heartbeat fluctuation high frequency component power (time series) are outputted to the sleepiness detecting section 23D.

According to the heart rate (RR interval) acquired by the heartbeat signal preprocessing section 21 and the heartbeat fluctuation low frequency component power (time series) acquired by the feature amount extracting section 22D, the threshold setting section 27 sets a threshold for judging whether or not sleepiness occurs in the driver. Hence, the threshold setting section 27 functions as the threshold setting means recited in the claims. The threshold set by the threshold setting section 27 is outputted to the sleepiness detecting section 23D.

A method for setting a threshold will now be explained with reference to a case of setting the second sleepiness judging threshold D2, by way of example. The method for setting the first sleepiness judging threshold D1 is identical or similar to that for the second sleepiness judging threshold D1 and thus will not be explained here.

Examples of the method for setting the second sleepiness judging threshold D2 include those switching a plurality of preset thresholds according to changing states of the heart rate (RR interval) and changing states of the heartbeat fluctuation low frequency component power, and those based on arithmetic operations.

First, with reference to FIG. 23, a method for switching among a plurality of preset thresholds will be explained. FIG. 23 is a table showing relationships among the heart rate, low frequency component of a heartbeat fluctuation, and set thresholds. In this case, as shown in FIG. 23, four preset thresholds D2A, D2B, D2C, and D2D are switched according to changing states of the heart rate and changing states of the heartbeat fluctuation low frequency component power. The threshold D2A is selected in the state (1) where the heart rate increases or decreases while the heartbeat fluctuation low frequency component power increases. The threshold D213 is selected in the state (2) where the heart rate increases or decreases while the heartbeat fluctuation low frequency component power is unchanged or decreases. The threshold D2C is selected in the state (3) where the heart rate is unchanged while the heartbeat fluctuation low frequency component power increases. The threshold D2D is selected in the state (4) where the heart rate does not change while the heartbeat fluctuation low frequency component power is unchanged or decreases. Here, the four thresholds D2A, D2B, D2C, and D2D have relationships of D2A>D2C>D2B>D2D.

A method for judging whether the heart rate and heartbeat fluctuation low frequency component power increase or decrease will now be explained. Examples of the method for judging whether the heart rate and heartbeat fluctuation low frequency component power increase or decrease include those based on statistical tests and those judging from the gradient of the interval data time series.

Figure 24:
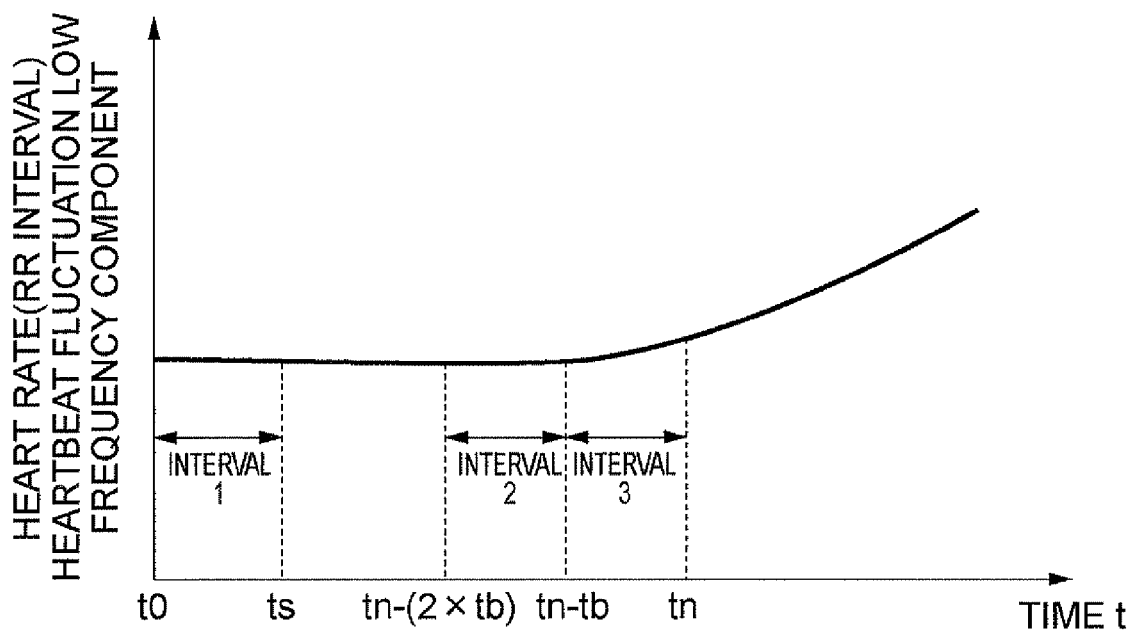
FIG. 24 is a diagram showing a method for judging whether or not the heart rate and low frequency component of a heartbeat fluctuation increase/decrease.

First, with reference to FIG. 24, a method based on a statistical test will be explained. The abscissa of FIG. 24 indicates the time t (sec) passed from a detection start time, while the ordinate indicates the heart rate or heartbeat fluctuation low frequency component power. In FIG. 24, t0 is a sleepiness detection start time, while ts is a given time for defining an interval 1. On the other hand, tn is the present time, while tb is a given time for defining intervals 2 and 3. This method compares the intervals shown in FIG. 24 with each other by a statistical test, thereby judging whether or not the heart rate or heartbeat fluctuation low frequency component power increases/decreases. Here, combinations of the intervals to be tested include the combination of intervals 1 and 3, the combination of intervals 2 and 3, and the like; the test is carried out between the intervals in each combination.

The following is a hypothesis at the time of the test. A case where data included in both intervals are extracted from groups having the same distribution is taken as a null hypothesis H0, while a case where data included in both intervals are extracted from groups having different distributions is taken as an alternative hypothesis H1. When the null hypothesis H0 is adopted by the test, it can be determined that no significant difference exists between both intervals, whereby it is judged that the heart rate or heartbeat fluctuation low frequency component power has no change (no increase/decrease). When the alternative hypothesis H1 is adopted by the test, on the other hand, it can be determined that a significant difference exists between both intervals, whereby it is judged that the heart rate or heartbeat fluctuation low frequency component power is increased or decreased.

A method for judging whether or not the heart rate and heartbeat fluctuation low frequency component power increase or decrease from the gradient of the interval data time series will now be explained. This method determines the gradient of the data time series in each interval shown in the above-mentioned FIG. 24 and judges whether or not the heart rate and heartbeat fluctuation low frequency component power increase or decrease from the gradient. As a method for determining the gradient, a simple linear regression calculation or the like can be used, for example.

For example, a simple linear regression calculation is carried out for the interval 3, so as to determine a gradient B, and it can be judged that there is an increase or decrease when the absolute value of the gradient B is greater than a gradient threshold α (|B|>α). The gradient threshold α is a constant which can be set arbitrarily.

Also, a simple linear regression calculation may be carried out for the intervals 1 and 3, so as to determine respective gradients A and B of the intervals 1 and 3, whereby it can be judged that an increase/decrease exists when the gradient B is greater than the gradient A (B>A), no change (no increase/decrease) exists when the gradient B and A are identical to each other (B=A), and a decrease/increase exists when the gradient A is greater than the gradient B (B<A). Here, it may be judged that an increase/decrease exists when the absolute value of the difference between the gradients B and A is greater than a difference amount judging threshold γ (|B−A|>γ). The difference amount judging threshold γ is a constant which is set arbitrarily.

A method based on an arithmetic operation will now be explained. In this case, the second sleepiness judging threshold D2 is determined by the following expression (1):

$$D2 = M + (b \times SD) \quad (1)$$

where b denotes a coefficient, M denotes an interval average value of the heartbeat fluctuation low frequency component power, and SD denotes an interval standard deviation of the heartbeat fluctuation low frequency component power.

Similarly, the first sleepiness judging threshold D1 is determined by the following expression (2):

$$D1 = M + (a \times SD) \quad (2)$$

where a is a coefficient satisfying a<b.

When the heartbeat fluctuation low frequency component power acquired by the feature amount extracting section 22D is greater than the heartbeat fluctuation high frequency component power, the sleepiness detecting section 23D judges whether or not sleepiness occurs in the driver (i.e., the degree of awakening of the driver) according to the heartbeat fluctuation low frequency component power (time series). More specifically, when the heartbeat fluctuation low frequency component power is not greater than the first sleepiness judging threshold D1 set by the threshold setting section 27, it is judged to be a state without sleepiness. When the heartbeat fluctuation low frequency component power is greater than the first sleepiness judging threshold D1 but not greater than the second sleepiness judging threshold D2, it is judged to be a state with weak sleepiness (state where the degree of awakening is lowered slightly). When the heartbeat fluctuation low frequency component power is greater than the second sleepiness judging threshold D2 set by the threshold setting section 27, it is judged to be a state with strong sleepiness (state where the degree of awakening is lowered greatly). Here, the second sleepiness judging threshold D2>the first sleepiness judging threshold D1. Thus, the sleepiness detecting section 23D also functions as the judging means recited in the claims and executes the judging step.

Figure 21:
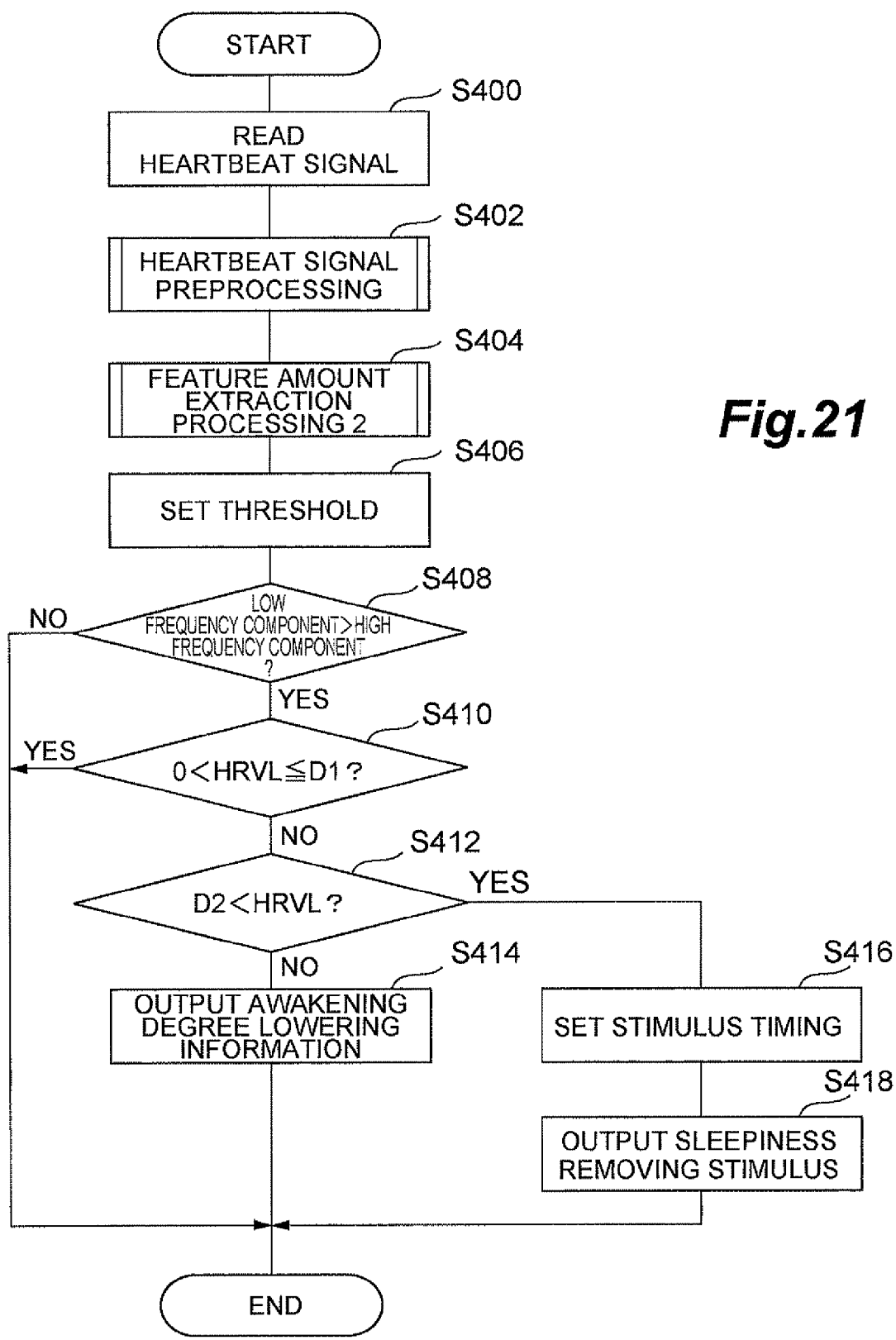
FIG. 21 is a flowchart showing a procedure of processing for detecting lowering of the degree of awakening by the device for judging a degree of awakening in accordance with the second embodiment.

With reference to FIG. 21, operations of the device for judging a degree of awakening 2 and the method for judging a degree of awakening will now be explained. FIG. 21 is a flowchart showing a procedure of processing for detecting lowering of the degree of awakening by the device for judging a degree of awakening 2. This processing, which is carried out by the ECU 20D, is repeatedly executed at a predetermined timing before the power of the ECU 20D is turned off after being turned on.

Since steps S400 and S402 are identical to the above-mentioned steps S100 and S102, respectively, their overlapping explanations will be omitted here.

Figure 22:
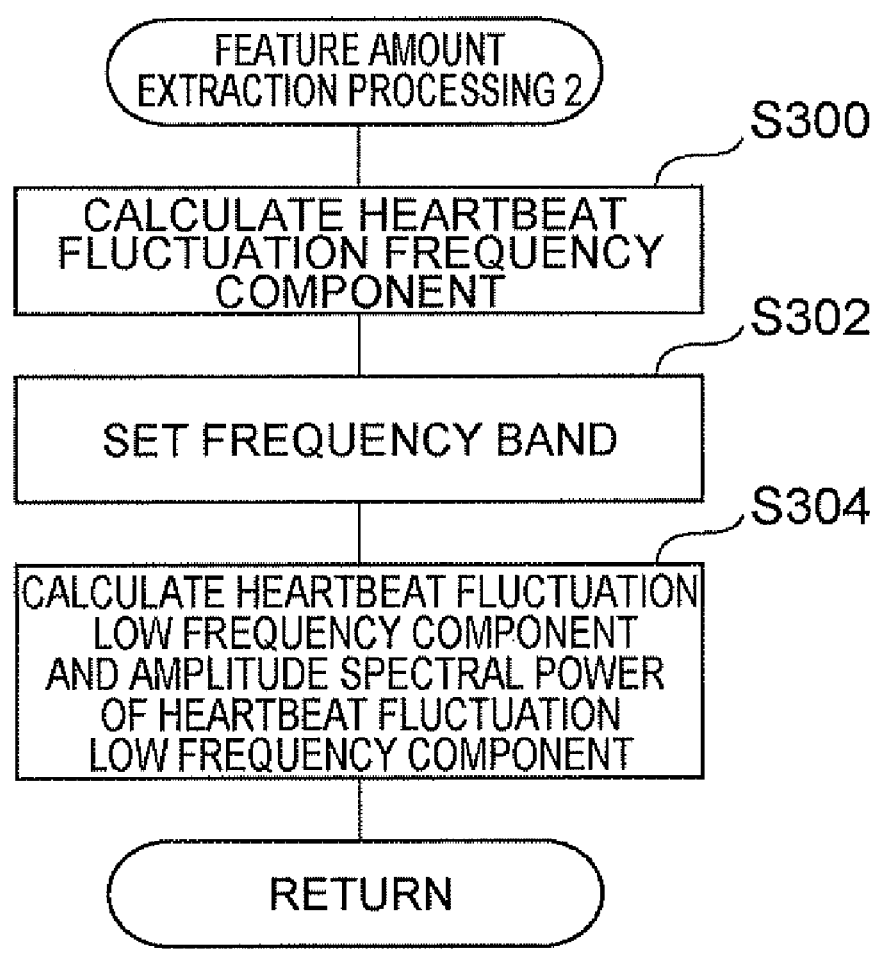
FIG. 22 is a flowchart showing a procedure of feature amount extraction processing in the processing for detecting lowering of the degree of awakening.

At subsequent step S404, feature amount extraction processing 2 for acquiring a heartbeat fluctuation low frequency component power (time series) and a heartbeat fluctuation high frequency component power (time series) from the heartbeat period time series data is executed. The feature amount extraction processing 2 will now be explained with reference to FIG. 22.

First, at step S500, the heartbeat period time series data in an analysis unit interval width Tterm (sec) prior to a reference time T which is a given timestamp is subjected to fast Fourier transform (FFT) processing as in the above-mentioned step S300.

At subsequent step S502, in the power spectrum obtained for each analysis unit interval by the FFT processing, an amplitude spectrum is integrated in a frequency band of a low frequency component (around 0.1 Hz), and an amplitude spectrum is integrated in a frequency band of a high frequency component (around 0.3 Hz).

At subsequent step S504, processing of subjecting the heartbeat period time series data in the analysis unit interval width Tterm to the FET processing and integrating the resulting power spectrum is repeated at each reference time after the lapse of a predetermined time. Consequently, a heartbeat fluctuation low frequency component power (time series) and a heartbeat fluctuation high frequency component power (time series) are acquired. Thereafter, the processing shifts to step S406 shown in FIG. 21.

At step S406, a threshold for judging whether or not sleepiness occurs in the driver is set according to the heart rate (RR interval) and the heartbeat fluctuation low frequency component power (time series). Since the method for setting the threshold is as mentioned above, overlapping explanations will be omitted here.

At subsequent step S408, it is judged whether the heartbeat fluctuation low frequency component power is greater than the heartbeat fluctuation high frequency component power or not. When the heartbeat fluctuation low frequency component power is greater than the heartbeat fluctuation high frequency component power here, the processing shifts to step S410. When the heartbeat fluctuation low frequency component power is not greater than the heartbeat fluctuation high frequency component power, on the other hand, it is judged to be an exceptional case, whereby the processing is once broken.

At subsequent step S410, it is judged whether or not the heartbeat fluctuation low frequency component power is greater than 0 and not greater than the first sleepiness judging threshold D1 set at step S406. When the heartbeat fluctuation low frequency component power is not greater the first sleepiness judging threshold D1 here, it is judged to be a state without sleepiness, whereby the processing is once broken. When the heartbeat fluctuation low frequency component power is greater than the first sleepiness judging threshold D1, on the other hand, the processing shifts to step S412.

At step S412, it is judged whether or not the heartbeat fluctuation low frequency component power is greater than the second sleepiness judging threshold D2 set at step S406. When the heartbeat fluctuation low frequency component power is not greater than the second sleepiness judging threshold D2 here, it is judged to be a state with weak sleepiness (state where the degree of awakening is lowered slightly), whereby the processing shifts to step S414. When the heartbeat fluctuation low frequency component power HRVL is greater than the second sleepiness judging threshold D2, on the other hand, it is judged to be a state with strong sleepiness (state where the degree of awakening is lowered greatly), whereby the processing shifts to step S416.

Steps S414, S416, and S418 are identical to steps S110, S112, and S114, respectively, and thus will not be explained here.

As mentioned above, the activity of the sympathetic nerve system is energized in the state of acting against sleepiness. Here, the activity of the parasympathetic nerve system usually decreases. However, there is an exceptional case where the activity of the parasympathetic nerve system increases together with the activity of the sympathetic nerve system. This embodiment judges whether the degree of awakening is lowered or not when the heartbeat fluctuation low frequency component power, which is a physiological index correlated with the sympathetic activity, is greater than the heartbeat fluctuation high frequency component power, which is a physiological index correlated with the parasympathetic activity, and thus can accurately detect the state of truly acting against sleepiness while excluding the above-mentioned exceptional case.

Preferably, the threshold for judging whether the degree of awakening of the person is lowered or not is changed according to individual differences, changes in physical conditions in the day even in the case of the same person, or the like, for example. This embodiment sets a threshold according to the heartbeat signal and heartbeat fluctuation low frequency component power, and judges that the degree of awakening is lowered when the heartbeat fluctuation low frequency component power is greater than the threshold. Therefore, the threshold can be set in conformity to physiological characteristics of each driver, whereby the accuracy in sleepiness detection can be improved.

EXAMPLE 5

Figure 25:
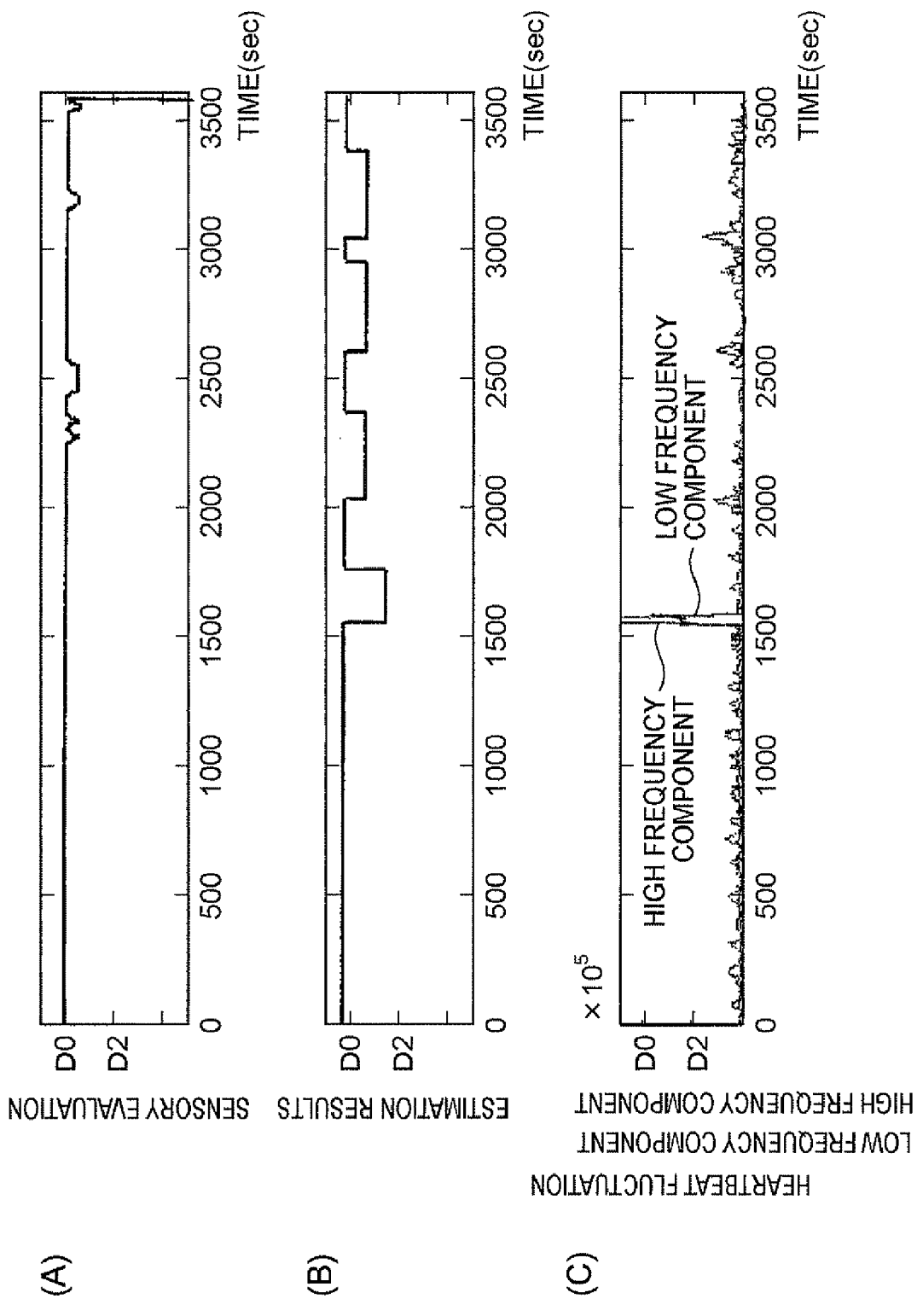
FIG. 25 is a diagram showing an example of sleepiness detection results in a case where a heartbeat fluctuation high frequency component power is not taken into consideration.
Figure 26:
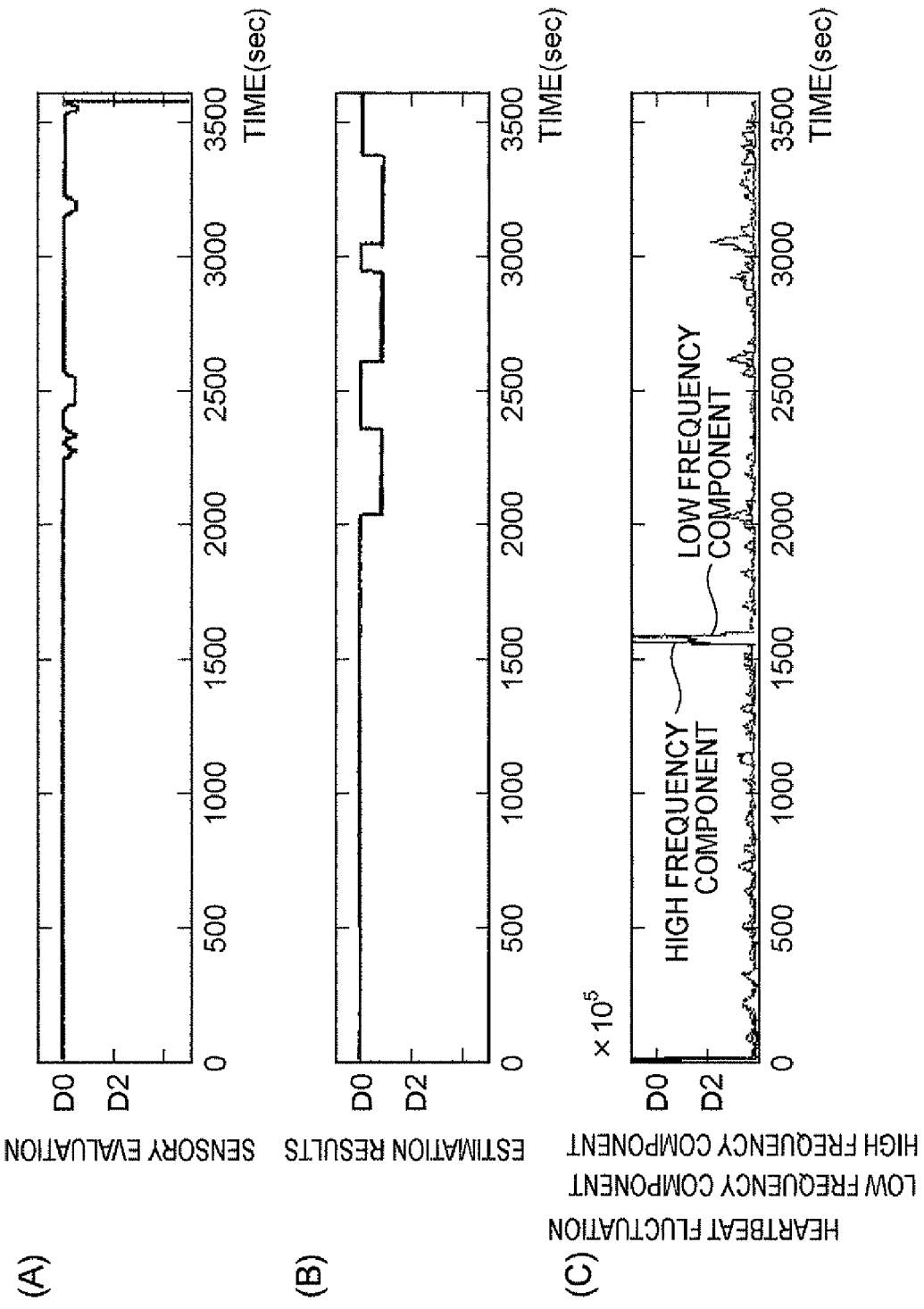
FIG. 26 is a diagram showing an example of sleepiness detection results in a case where the heartbeat fluctuation high frequency component power is taken into consideration.

As a functional evaluation test of the above-mentioned device for judging a degree of awakening 2, a test for detecting lowering of awakening was carried out in cases where the heartbeat fluctuation high frequency component power was taken into consideration and not. The test results will be explained with reference to FIGS. 25 and 26. FIG. 25 is a diagram showing an example of sleepiness detection results in the case where the heartbeat fluctuation high frequency component power was not taken into consideration. On the other hand, FIG. 26 is a diagram showing an example of sleepiness detection results in the case where the heartbeat fluctuation high frequency component power was taken into consideration. In each of FIGS. 25 and 26, the abscissa indicates the lapse of time (sec), while the ordinate indicates (A) sensory evaluation results, (B) sleepiness detection results (estimation results), and (C) heartbeat fluctuation low frequency component power/heartbeat fluctuation high frequency component power in order from the upper side.

In the case where the heartbeat fluctuation high frequency component power is not taken into consideration, i.e., the case where it is judged to be a state with strong sleepiness simply when the heartbeat fluctuation low frequency component power exceeds the second sleepiness judging threshold D2, it is judged to be a state with strong sleepiness when the heartbeat fluctuation low frequency component power increases at a lapse of time of about 1500 sec as shown in the middle part of FIG. 25. At this time, however, the heartbeat fluctuation high frequency component power also increases, so that this does not seem to be a state where the degree of awakening of the driver is truly lowered, but an exceptional case where the activity of the parasympathetic nerve system increases together with the activity of the sympathetic nerve system, such as a case where the driver is startled or a change occurs in an environment such as air-conditioning. Therefore, the sensory evaluation shown in the upper part (A) of FIG. 25 does not detect sleepiness. That is, such an exceptional case cannot be excluded when the heartbeat fluctuation high frequency component power is not taken into consideration.

In the case where the heartbeat fluctuation high frequency component power is taken into consideration, i.e., the case where it is judged to be a state with strong sleepiness when the heartbeat fluctuation low frequency component power is greater than the heartbeat fluctuation high frequency component power while the heartbeat fluctuation low frequency component power exceeds the second sleepiness judging threshold D2, on the other hand, it is not judged to be a state with sleepiness when the heartbeat fluctuation low frequency component power increases after a lapse of about 1500 sec as shown in the middle part of FIG. 26. Thus taking account of the heartbeat fluctuation high frequency component power was able to exclude the exceptional case where the activity of the parasympathetic nerve system increased together with the activity of the sympathetic nerve system, whereby the effectiveness of the present invention has been verified.

EXAMPLE 6

Figure 27:
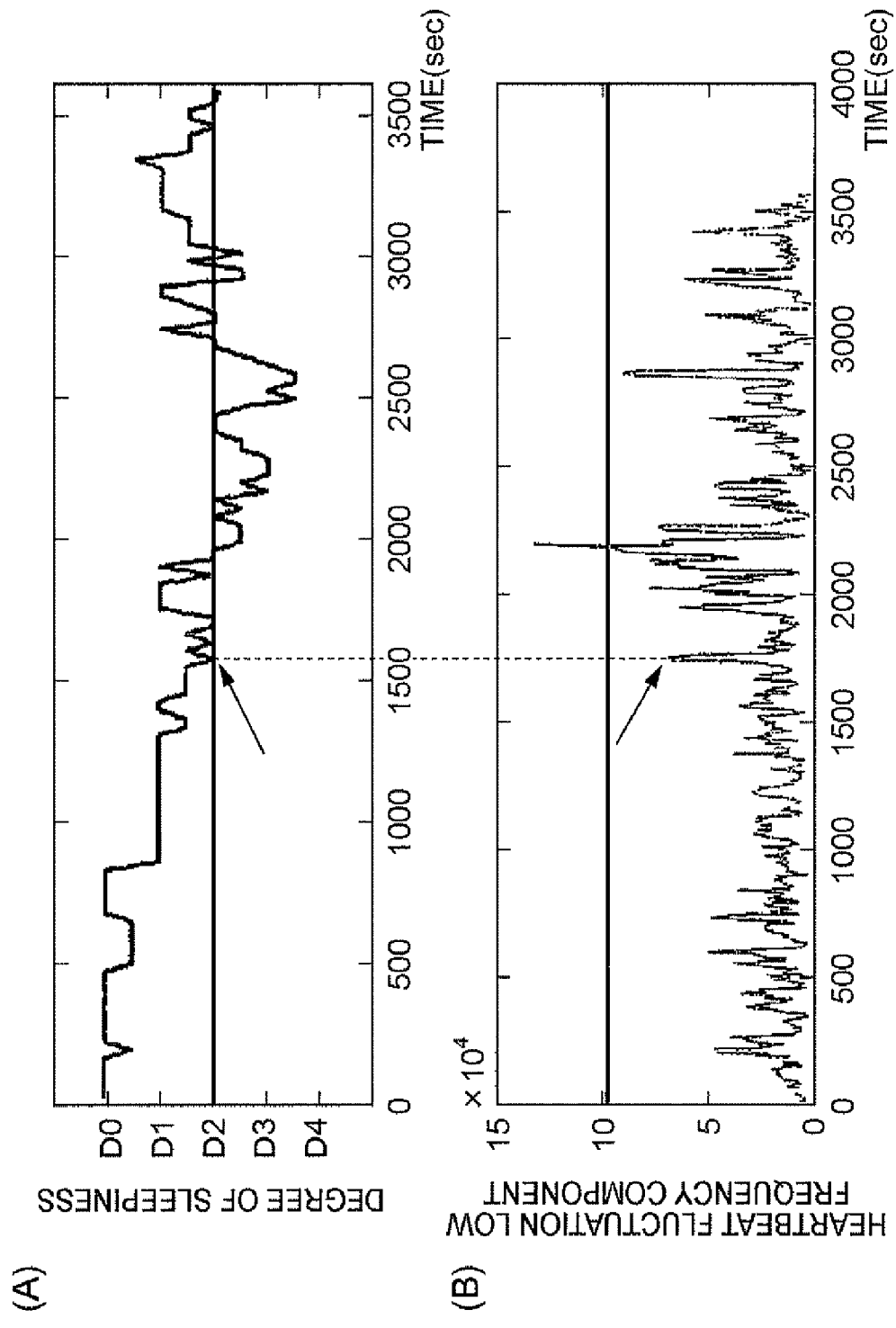
FIG. 27 is a diagram showing sleepiness detection results obtained when a sleepiness judging threshold is fixed.

As a functional evaluation test of the above-mentioned device for judging a degree of awakening 2, a test for detecting lowering of awakening was carried out in cases where a sleepiness judging threshold was fixed and not. The test results will be explained with reference to FIGS. 27 and 28. FIG. 27 is a diagram showing an example of sleepiness detection results in the case where the sleepiness judging threshold was fixed. On the other hand, FIG. 28 is a diagram showing an example of sleepiness detection results in the case where the sleepiness judging threshold was made variable. In each of FIGS. 27 and 28, the abscissa indicates the lapse of time (see), while the ordinate indicates (A) the degree of sleepiness by the sensory evaluation and (B) heartbeat fluctuation low frequency component in order from the upper side.

As shown in FIG. 27, when it is judged by the sensory evaluation that strong sleepiness exists at a lapse of time of about 1600 sec (see an arrow in the diagram), the heartbeat fluctuation low frequency component power is less than the second sleepiness judging threshold D2 in the case where the sleepiness judging threshold is fixed, whereby it is not judged to be a state with strong sleepiness. Thus, the case where the sleepiness judging threshold is fixed is hard to flexibly respond to individual differences, changes in physical conditions, and the like in the drivers.

In the case where the sleepiness judging threshold is made variable, on the other hand, the heartbeat fluctuation low frequency component power exceeds the changed second sleepiness judging threshold D2 when it is judged by the sensory evaluation that strong sleepiness exists at a lapse of time of about 1600 sec as shown in FIG. 28 (see an arrow in the diagram). Thus varying the sleepiness judging thresholds was able to carry out sleepiness detection in conformity to physiological characteristics of the driver, whereby the effectiveness of the present invention has been verified.

EXAMPLE 7

As a functional evaluation test of the above-mentioned device for judging a degree of awakening 2, a second sleepiness judging threshold changing test was carried out. The test results will be explained with reference to FIG. 29. FIG. 29 is a diagram showing an example of results of changing the sleepiness judging threshold. In FIG. 29, the abscissa indicates the lapse of time (sec), while the ordinate indicates (A)

the heartbeat fluctuation low frequency component power and (B) heart rate in order from the upper side.

As the threshold setting method, the above-mentioned method based on the statistical test was used. As a result of testing for the heartbeat fluctuation low frequency component power and heart rate in the intervals 1 and 2 in FIG. 29, it was judged that no significant difference was found in the heartbeat fluctuation low frequency component power, while a significant difference was found (P<0.005) in the heart rate. According to these test results, it was decided to change the sleepiness judging threshold. As the method for setting the sleepiness judging thresholds, the above-mentioned method based on the arithmetic operation was used. That is, an interval average value M (=21300) of the heartbeat fluctuation low frequency component power in the interval 2 and an interval standard deviation SD (=6400) of the heartbeat fluctuation low frequency component power were put into the above-mentioned expression (2), so as to determine the second sleepiness judging threshold D2 (=40500). Here, the coefficient b=3.

As a result, as shown in the upper part (A) of FIG. 29, the second sleepiness judging threshold D2 was changed from $10 \times 10^4$ to $4.05 \times 10^4$ at the time when the interval 2 ended. Thus, it has been verified that the sleepiness judging threshold is appropriately changed according to the heartbeat fluctuation low frequency component power and heart rate.

Though embodiments of the present invention have been explained in the foregoing, the present invention can be modified in various ways without being restricted to the above-mentioned embodiments. For example, the place for mounting the device for judging a degree of awakening is not limited to vehicles, while the subject for which the lowering of the degree of awakening is carried out is not limited to drivers of vehicles. Hence, the present invention is applicable to health appliances, medical appliances, and the like.

As the sensor for acquiring the heartbeat signal of the driver, not only potentiometric heartbeat sensors, but also infrared heartbeat sensors which detect the infrared reflected light quantity periodically changing in response to heartbeats, sensors for detecting the blood pressure of the driver, and the like can be used.

Though the levels of the degree of awakening detected by the device for judging a degree of awakening 1 is classified into three stages in the above-mentioned embodiments, they may be two stages or four or more stages.

Industrial Applicability

Since the device and method for judging a degree of awakening are constructed such as to acquire a physiological index indicating a strength of a state of acting against sleepiness from a biological signal of a person in action and judge the degree of awakening according to the physiological index, the present invention can more accurately detect weak sleepiness of the person in action.

The invention claimed is:

1. A device for judging a degree of awakening, the device comprising:
    signal acquiring means for acquiring a biological signal of a person in action;
    index acquiring means for acquiring a physiological index indicating a strength of a state of acting against sleepiness from the biological signal;
    judging means for judging the degree of awakening of the person according to the physiological index;
    stimulus providing means for imparting a stimulus for raising the degree of awakening of the person; and
    timing setting means for setting a timing for providing the stimulus before a predetermined time passes after the physiological index exceeds a predetermined value, wherein
    the biological signal is a heartbeat signal, and
    the physiological index comprises an amplitude spectral power of a heartbeat fluctuation low frequency component acquired from the heartbeat signal.

2. The device for judging a degree of awakening according to claim 1, wherein the physiological index is correlated with a sympathetic activity.

3. The device for judging a degree of awakening according to claim 1, wherein the judging means judges that the degree of awakening is lowered when the amplitude spectral power of the heartbeat fluctuation low frequency component is greater than a first predetermined value.

4. The device for judging a degree of awakening according to claim 3, wherein the judging means judges that the degree of awakening is further lowered when the amplitude spectral power of the heartbeat fluctuation low frequency component is greater than both the first predetermined value and a second predetermined value.

5. The device for judging a degree of awakening according to claim 1, wherein
    the timing setting means provides the stimulus according to the physiological index indicating the strength of the state of acting against the sleepiness.

6. The device for judging a degree of awakening according to claim 1, wherein the physiological index corresponds to a time between a time when a heartbeat fluctuation low frequency component power exceeds a predetermined value and a time when the heartbeat fluctuation low frequency component power becomes lower than the predetermined value or at a time when the heartbeat fluctuation low frequency component power attains a local minimum.

7. A device for judging a degree of awakening, the device comprising:
    signal acquiring means for acquiring a biological signal of a person in action;
    index acquiring means for acquiring a physiological index indicating a strength of a state of acting against sleepiness from the biological signal;
    judging means for judging the degree of awakening of the person according to the physiological index;
    stimulus providing means for imparting a stimulus for raising the degree of awakening of the person; and
    timing setting means for setting a timing for providing the stimulus before the amplitude spectral power of the heartbeat fluctuation low frequency component attains the nearest local minimum after exceeding a predetermined value, wherein
    the biological signal is a heartbeat signal, and
    the physiological index is an amplitude spectral power of a heartbeat fluctuation low frequency component acquired from the heartbeat signal.

8. A method for judging a degree of awakening, the method comprising:
    a signal acquiring step of acquiring a biological signal of a person in action;
    an index acquiring step of acquiring a physiological index indicating a strength of a state of acting against sleepiness from the biological signal;
    a judging step of judging the degree of awakening of the person according to the physiological index;
    a stimulus providing step of imparting a stimulus for raising the degree of awakening of the person; and a timing setting step of setting a timing for providing the stimulus before a predetermined time passes after the physiological index exceeds a predetermined value, wherein the biological signal is a heartbeat signal, and the physiological index comprises an amplitude spectral power of a heartbeat fluctuation low frequency component acquired from the heartbeat signal.

9. The method for judging a degree of awakening according to claim 8, wherein the physiological index is correlated with a sympathetic activity.

10. The method for judging a degree of awakening according to claim 8, wherein the judging step judges that the degree of awakening is lowered when the amplitude spectral power of the heartbeat fluctuation low frequency component is greater than a first predetermined value.

11. The method for judging a degree of awakening according to claim 10, wherein the judging step judges that the degree of awakening is further lowered when the amplitude spectral power of the heartbeat fluctuation low frequency component is greater than both the first predetermined value and a second predetermined value.

12. The method for judging a degree of awakening according to one of claim 8, wherein the timing setting step provides the stimulus according to the physiological index indicating the strength of the state of acting against the sleepiness.

13. The method for judging a degree of awakening according to claim 8, wherein the physiological index corresponds to a time between a time when a heartbeat fluctuation low frequency component power exceeds a predetermined value and a time when the heartbeat fluctuation low frequency component power becomes lower than the predetermined value or at a time when the heartbeat fluctuation low frequency component power attains a local minimum.

14. The method for judging a degree of awakening according to claim 8, wherein the physiological index further comprises at least one portion that is correlated with a sympathetic activity and at least one portion that is correlated with a parasympathetic activity.

15. The method for judging a degree of awakening according to claim 14, wherein the physiological index comprises respective amplitude spectral powers of heartbeat fluctuation high and low frequency components acquired from the heartbeat signal.

16. The method for judging a degree of awakening according to claim 15, wherein the judging step judges whether or not the degree of awakening of the person is lowered when the amplitude spectral power of the heartbeat fluctuation low frequency component is greater than the amplitude spectral power of the heartbeat fluctuation high frequency component.

17. The method for judging a degree of awakening according to claim 16, further comprising:

a threshold setting step of setting a threshold for judging whether the degree of awakening of the person is lowered or not;

wherein the judging step judges that the degree of awakening of the person is lowered when the amplitude spectral power of the heartbeat fluctuation low frequency component is greater than the threshold.

18. The method for judging a degree of awakening according to claim 17, wherein the threshold setting step sets the threshold according to the heartbeat signal and the amplitude spectral power of the heartbeat fluctuation low frequency component.

19. A method for judging a degree of awakening, the method comprising:

a signal acquiring step of acquiring a biological signal of a person in action;

an index acquiring step of acquiring a physiological index indicating a strength of a state of acting against sleepiness from the biological signal;

a judging step of judging the degree of awakening of the person according to the physiological index;

a stimulus providing step of imparting a stimulus for raising the degree of awakening of the person; and a timing setting step of setting a timing for providing the stimulus before the amplitude spectral power of the heartbeat fluctuation low frequency component attains the nearest local minimum after exceeding a predetermined value, wherein the biological signal is a heartbeat signal; and the physiological index is an amplitude spectral power of a heartbeat fluctuation low frequency component acquired from the heartbeat signal.

20. The device for judging a degree of awakening according to claim 1, wherein the physiological index further comprises at least one portion that is correlated with a sympathetic activity and at least one portion that is correlated with a parasympathetic activity.

21. The device for judging a degree of awakening according to claim 20, wherein the physiological index comprises respective amplitude spectral powers of heartbeat fluctuation high and low frequency components acquired from the heartbeat signal.

22. The device for judging a degree of awakening according to claim 21, wherein the judging means judges whether the degree of awakening is lowered or not when the amplitude spectral power of the heartbeat fluctuation low frequency component is greater than the amplitude spectral power of the heartbeat fluctuation high frequency component.

23. The device for judging a degree of awakening according to claim 22, further comprising:

threshold setting means for setting a threshold for judging whether the degree of awakening of the person is lowered or not;

wherein the judging means judges that the degree of awakening of the person is lowered when the amplitude spectral power of the heartbeat fluctuation low frequency component is greater than the threshold.

24. The device for judging a degree of awakening according to claim 22, wherein the threshold setting means sets the threshold according to the heartbeat signal and the amplitude spectral power of the heartbeat fluctuation low frequency component.

* * * * *